(12) United States Patent
Lin et al.

(10) Patent No.: US 10,222,381 B2
(45) Date of Patent: Mar. 5, 2019

(54) WATER-SOLUBLE PEPTIDE FLUORESCENCE MATERIAL

(71) Applicant: NATIONAL CHIAO TUNG UNIVERSITY, Hsinchu (TW)

(72) Inventors: Hsin-Chieh Lin, Hsinchu (TW); Shu-Min Hsu, Taichung (TW)

(73) Assignee: NATIONAL CHIAO TUNG UNIVERSITY, Hsinchu (TW)

( * ) Notice: Subject to any disclaimer, the term of this patent is extended or adjusted under 35 U.S.C. 154(b) by 0 days.

(21) Appl. No.: 15/083,298

(22) Filed: Mar. 29, 2016

(65) Prior Publication Data

US 2018/0052170 A1   Feb. 22, 2018

(30) Foreign Application Priority Data

Dec. 1, 2015 (TW) ............... 104140184 A

(51) Int. Cl.
| | |
|---|---|
| C07K 7/06 | (2006.01) |
| C09K 11/06 | (2006.01) |
| G01N 33/58 | (2006.01) |
| C07K 5/097 | (2006.01) |
| C07K 5/117 | (2006.01) |
| C07K 5/107 | (2006.01) |

(52) U.S. Cl.
CPC ......... *G01N 33/582* (2013.01); *C07K 5/0821* (2013.01); *C07K 5/1016* (2013.01); *C07K 5/1024* (2013.01); *C07K 7/06* (2013.01); *C09K 11/06* (2013.01); *C09K 2211/1007* (2013.01); *C09K 2211/1011* (2013.01); *C09K 2211/1029* (2013.01)

(58) Field of Classification Search
CPC .. G01N 33/582; C07K 5/0821; C07K 5/1024; C07K 7/06; C07K 11/06
USPC ........................................................ 546/110
See application file for complete search history.

(56) References Cited

U.S. PATENT DOCUMENTS

| | | | |
|---|---|---|---|
| 6,225,052 B1 * | 5/2001 | Batz ................... | C07H 21/00 435/287.2 |
| 6,830,889 B1 | 12/2004 | Matsumoto et al. | |
| 8,354,499 B2 | 1/2013 | Mayer-Cumblidge et al. | |
| 8,440,835 B2 | 5/2013 | Imperiali et al. | |
| 2012/0282703 A1 | 11/2012 | Tang et al. | |
| 2013/0266953 A1 | 10/2013 | Tang et al. | |

FOREIGN PATENT DOCUMENTS

| | | |
|---|---|---|
| CN | 102504105 B | 10/2013 |
| CN | 103739549 A | 4/2014 |

OTHER PUBLICATIONS

Eva Engel et al., "Light-Induced Decomposition of Indocyanine Green", Investigative Ophthalmology & Visual Science, May 2008, vol. 49, No. 5, pp. 1777-1783.
Yuning Hong et al., "Water-Soluble Tetraphenylethene Derivatives as Fluorescent "Light-Up" Probes for Nucleic Acid Detection and Their Applications in Cell Imaging", Chemistry an Asian Journal, Aug. 2013, pp. 1806-1812.
Yanqing Tian et al., "A series of naphthalimide derivatives as intra and extracellular pH sensors", Biomaterials, 2010, pp. 7411-7422.
Melek Baglan et al., "Selective and sensitive turn-on fluorescent sensing of arsenite based on cysteine fused tetraphenylethene with AIE characteristics in aqueous media", Chem. Commun., 2013, pp. 5325-5327.

(Continued)

*Primary Examiner* — Rita J Desai
(74) *Attorney, Agent, or Firm* — CKC & Partners Co., LLC

(57) ABSTRACT

A water-soluble peptide fluorescence material having a structure of formula (I):

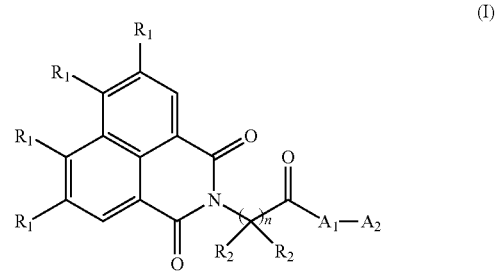

(I)

In formula (I), n is an integer greater than or equal to 1, $R_1$ is independently selected from hydrogen or a nitrogen-containing functional group, $R_2$ is independently selected from hydrogen or alkyl, and $A_1$ is polymerized by at least one amino acid monomer and having a structure of formula (II):

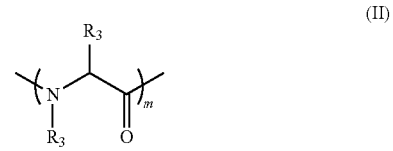

(II)

In formula (II), m is an integer greater than or equal to 1, and $R_3$ in each, of the amino acid monomers of $A_1$ is independently selected from hydrogen, alkyl, aralkyl, alkylthioaalkyl, hydroxyaralky, heteroaralkyl, carboxylalkyl, or guanidinylalkyl, $A_2$ is —$OR_5$ or —$N(R_4)_2$, and $R_4$ is independently selected from hydrogen, alkyl, aralkyl, alkylthioaalkyl, hydroxyaralky, heteroaralkyl, carboxylalkyl, guanidinylalkyl, monoglycosyl, biglycosyl, or oligosaccharyl, and $R_5$ is hydrogen, alkyl, aralkyl, alkylthioaalkyl, hydroxyaralky, heteroaralkyl, carboxylalkyl, or guanidinylalkyl.

5 Claims, 16 Drawing Sheets

Specification includes a Sequence Listing.

(56) References Cited

OTHER PUBLICATIONS

Bonnet CS et al., "Structural studies in aqueous solution of new binuclear lanthanide luminescent peptide conjugates", Chemical Communications, vol. 38, 2008, pp. 4552-4554.

Lee MH et al., "Direct fluorescence monitoring of the delivery and cellular uptake of a cancer-targeted RGD peptide-appended naphthalimide theragnostic prodrug", Journal of the American Chemical Society, 2012, pp. 12668-12674.

* cited by examiner

WATER-SOLUBLE PEPTIDE FLUORESCENCE MATERIAL

RELATED APPLICATIONS

This application claims priority to Taiwan Application Serial Number 104140184, filed Dec. 1, 2015, which is herein incorporated by reference.

BACKGROUND

Field of Disclosure

The present disclosure relates to a water-soluble peptide fluorescence material. More particularly, the present disclosure relates to a water-soluble peptide fluorescence material having a naphthalimide group.

Description of Related Art

Fluorescence probes have advantages of high sensitivity, fast and convenient, high temporal resolution and low costs, so it is universally applied in biology and medical research. Generally, indocyanine green is used as a fluorescent dye. However, indocyanine green under illumination breaks down to toxic substances, so a light should be shielded during the use. In addition, naphthalimide linking with diethylenediamine has higher fluorescence intensity, but it can only be used as a fluorescence probe of acidic cells. If a film for sensing extracellular pH value is desired, an additional initiator, such as azobisisobutyronitrile (AIBN), should be added in the above material and treated in nitrogen gas to perform a thermal polymerization.

In addition, various problems are existed in using these traditional fluorescence probes. For example, the generated fluorescence is easily to be reduced or quenched when the fluorescent dye are aggregated, so the fluorescence intensity is correspondingly decreased, or is even non-luminous to significantly decrease the detecting effects. In order to avoid the aggregation, a fluorescent molecule is generally under chemical modification to graft a bulky group, so as to build steric hindrance between fluorescent molecules. As such, it effectively avoids the aggregation of fluorescent molecules. However, grafting the bulky group requires multi-steps synthesis and has much higher costs.

SUMMARY

An aspect of the present disclosure provides a water-soluble peptide fluorescence material having a structure of formula (I):

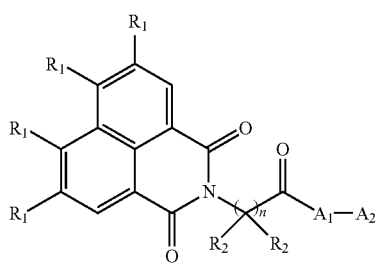

(I)

In formula (I), n is an integer greater than or equal to 1, $R_1$ is independently selected from hydrogen or a nitrogen-containing functional group, $R_2$ is independently selected from hydrogen or alkyl, and $A_1$ is polymerized by at least one amino acid monomer and having a structure of formula (II):

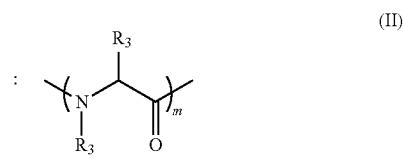

(II)

In formula (II), m is an integer greater than or equal to 1, and $R_3$ in each of the amino acid monomers of $A_1$ is independently selected from hydrogen, alkyl, aralkyl, alkylthioaalkyl, hydroxyaralky, heteroaralkyl, carboxylalkyl, or guanidinylalkyl. $A_2$ is $-OR_5$ or $-N(R_4)_2$, and $R_4$ is independently selected from hydrogen, alkyl, aralkyl, alkylthioaalkyl, hydroxyaralky, heteroaralkyl, carboxylalkyl, guanidinylalkyl, monoglycosyl, biglycosyl, or oligosaccharyl, and $R_5$ is hydrogen, alkyl, aralkyl, alkylthioaalkyl, hydroxyaralky, heteroaralkyl, carboxylalkyl, or guanidinylalkyl.

According to an embodiment of the present disclosure, $R_2$ is an alkyl group of 1-16 carbon atoms.

According to an embodiment of the present disclosure, $R_1$ is glucosamine, nitro group, pyrrolidine, piperidine, azepane or azocane.

According to an embodiment of the present disclosure, m is the integer of from 1 to 20.

According to an embodiment of the present disclosure, n is the integer of from 1 to 10.

According to an embodiment of the present disclosure, the monoglycosyl is fructosyl or galactosyl, the biglycosyl is mannosyl, and the oligosaccharyl is oligonucleic acid.

Another aspect of the present disclosure provides a method of preparing a water-soluble peptide fluorescence material, and the method includes following steps. A first amino acid monomer is grafted to a resin, and an amino group of the first amino acid monomer having a first protective group thereon, and the first protective group is removed from the amino group. A coupling agent is used to couple

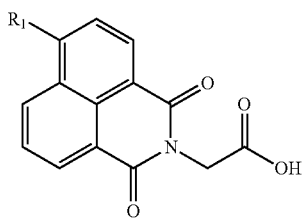

with the amino group to form the water-soluble peptide fluorescence material, and $R_1$ is independently selected from hydrogen or a nitrogen-containing functional group. Then, the water-soluble peptide fluorescence material is cleaved from the resin.

According to an embodiment of the present disclosure, the method further includes following steps after removing the first protective group. The coupling agent is used to couple a second amino acid monomer with the amino group of the first amino acid monomer, and an amino group of the second amino acid monomer has a second protective group thereon. Then, the second protective group is removed.

According to an embodiment of the present disclosure, nitrogen-containing functional group is glucosamine, nitro group, pyrrolidine, piperidine, azepane or azocane.

According to an embodiment of the present disclosure, the coupling agent includes O-(benzotriazol-1-yl)-N,N,N',N"-tetramethyluraniumhexafluorophosphate.

BRIEF DESCRIPTION OF THE DRAWINGS

The disclosure can be more fully understood by reading the following detailed description of the embodiment, with reference made to the accompanying drawings as follows.

DETAILED DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples. Therefore, the spirit and scope of the appended claims should not be limited to the description of the embodiments contained herein.

The present disclosure provides a water-soluble peptide fluorescence material, which has a characteristic of aggregation-induced emission (AIE) by changing a nitrogen heterocycle on naphthalimide, so as to prepare fluorescence dyes having different colors. In addition, an amino acid sequence grafted to the naphthalimide is changed to make the water-soluble peptide fluorescence material develop color in acid, neutral or weak base environment. The water-soluble peptide fluorescence material of the present disclosure has a structure of formula (I):

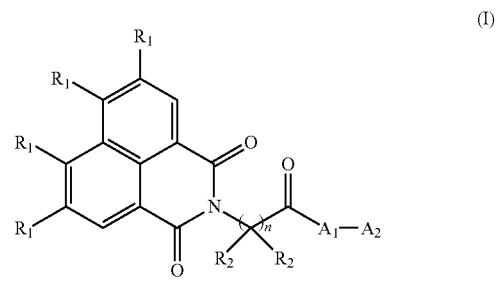

In formula (I), n is an integer greater than or equal to 1, $R_1$ is independently selected from hydrogen or a nitrogen-containing functional group, and $R_2$ is independently selected from hydrogen or alkyl. In some embodiments, the nitrogen-containing functional group is glucosamine, nitro group, pyrrolidine, piperidine, azepane or azocane. In some embodiments, $R_2$ is an alkyl group of 1-16 carbon atoms.

A1 of formula (I) is polymerized by at least one amino acid monomer and having a structure of formula (II):

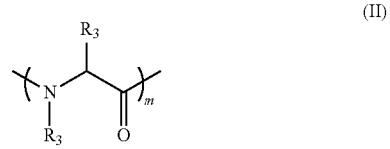

In formula (II), m is an integer greater than or equal to 1, and $R_3$ in each of the amino acid monomers of $A_1$ is independently selected from hydrogen, alkyl, aralkyl, alkylthioaalkyl, hydroxyaralky, heteroaralkyl, carboxylalkyl, or guanidinylalkyl. In some embodiments, the amino acid monomers of $A_1$ are the same. In various embodiments, the amino acid monomers of $A_1$ are different from each other.

Continuing in formula (I), $A_2$ thereof has a formula of —$OR_5$ or —$N(R_4)_2$. $R_4$ is independently selected from hydrogen, alkyl, aralkyl, alkylthioaalkyl, hydroxyaralky, heteroaralkyl, carboxylalkyl, guanidinylalkyl, monoglycosyl, biglycosyl, or oligosaccharyl, and $R_5$ is hydrogen, alkyl, aralkyl, alkylthioaalkyl, hydroxyaralky, heteroaralkyl, carboxylalkyl, or guanidinylalkyl. In some embodiments, the monoglycosyl is fructosyl or galactosyl, the biglycosyl is mannosyl, and the oligosaccharyl is oligonucleic acid.

In some embodiments, n is the integer of from 1 to 10, and m is the integer of from 1 to 20.

Figure 1C:
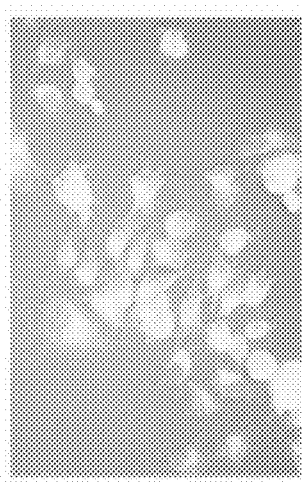
FIGS. 1A, 1B and 1C are comparative pictures between a water-soluble peptide fluorescence material of the present disclosure and a traditional fluorescence material at the same concentration.
Figure 1B:
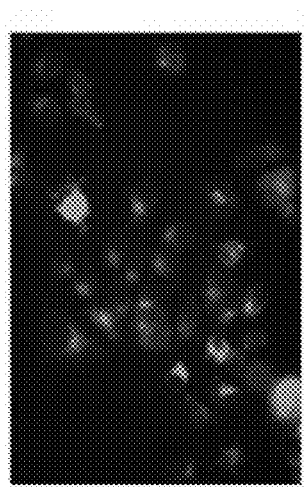
Figure 1A:

The water-soluble peptide fluorescence material is designed to illuminate in acid, neutral or weak base environment, and following embodiments give an example illuminating in acid environment. FIGS. 1A, 1B and 1C are comparative pictures between a water-soluble peptide fluorescence material of the present disclosure and a traditional fluorescence material at the same concentration. The water-soluble peptide fluorescence material has a structure of following formula including a peptide sequence Phe-Asp-Gly-Glu-Ala (SEQ ID NO: 5):

water-soluble peptide fluorescence material generates fluorescence at a cellular position substantially the same as Lysotracker. Accordingly, the water-soluble peptide fluorescence material is suitable for a biological fluorescence probe, so as to detect and mark positions of the acidic cells.

At the same concentration, the water-soluble peptide fluorescence material has the greater fluorescence intensity than that of Lysotracker. On this base, a dose of the water-soluble peptide fluorescence material could be decreased to achieve the same fluorescence intensity with the Lysotracker, so as to decrease medical costs and damage to human bodies.

Furthermore, the water-soluble peptide fluorescence material has a characteristic of aggregation-induced emission. The water-soluble peptide fluorescence material is placed in a co-solvent of water and organic solvent, and it is observed that the fluorescence intensity of the co-solvent is increased corresponding to a volume ratio of water. The amino acid of the water-soluble peptide fluorescence material has a hydrogen bond, which causes the characteristic of

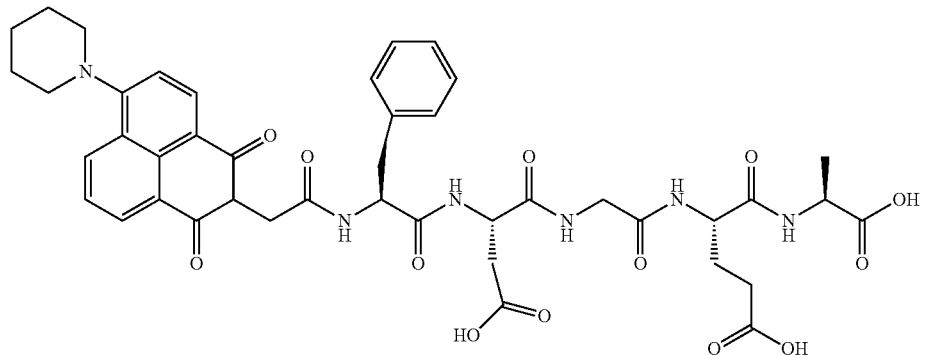 [SMILES: C[C@H](NC(=O)[C@H](CCC(=O)O)NC(=O)CNC(=O)[C@H](CC(=O)O)NC(=O)[C@H](Cc1ccccc1)NC(=O)CC1C(=O)c2cccc3c(N4CCCCC4)ccc(c23)C1=O)C(=O)O]

FIG. 1A uses a traditional, red fluorescence material, Lysotracker (Life Technologies), which is available in the market and used to mark acidic cells in living cells. As shown in FIG. 1A, Lysotracker appears red fluorescence at the acidic cells. Continuing in FIG. 1B to compare with FIG. 1A, FIG. 1B uses the water-soluble peptide fluorescence material of the present disclosure, which is also used to mark acidic cells in living cells. The water-soluble peptide fluorescence material appears green fluorescence at the acidic cells and has a fluorescence intensity greater than that of the red fluorescence of Lysotracker. FIG. 1C is an overlapped picture of FIG. 1A and FIG. 1B, which shows that the aggregation-induced emission in water to increase image contrast of cells, and thus has wide range of applications and easily to be operated.

Figure 2:
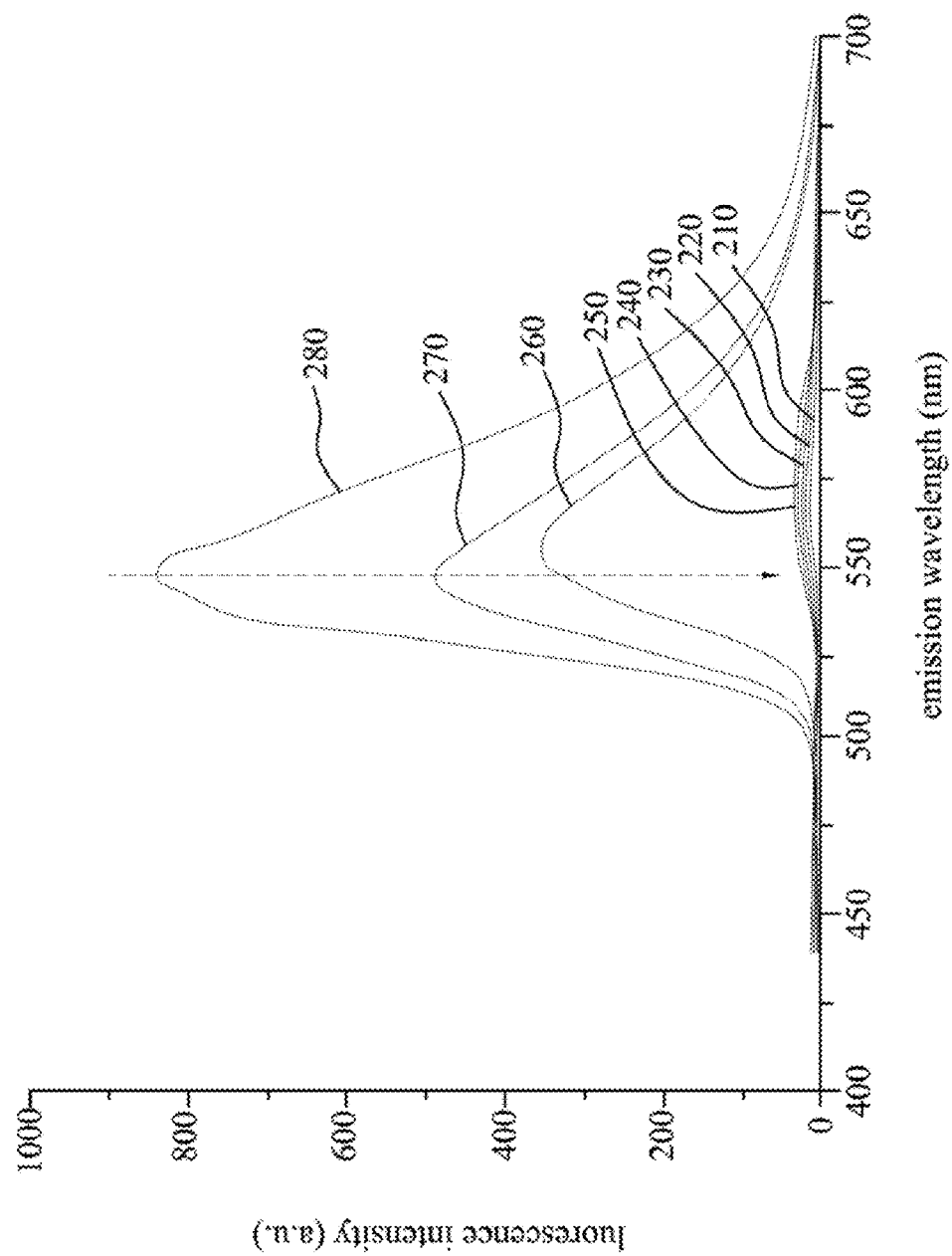
FIG. 2 illustrates a fluorescence intensity and an emission wavelength of the water-soluble peptide fluorescence material at different pH values.

FIG. 2 illustrates a fluorescence intensity and an emission wavelength of the water-soluble peptide fluorescence material at different pH values. The water-soluble peptide fluorescence material has a structure of following formula including a peptide sequence Phe-Asp-Gly-Glu-Ala (SEQ ID NO: 5):

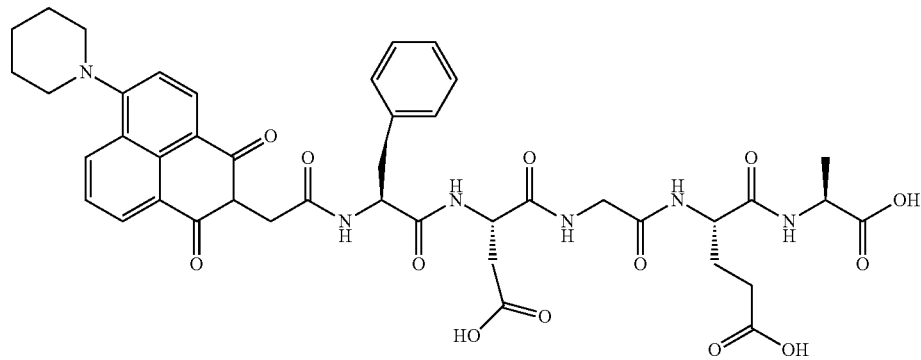 [SMILES: C[C@H](NC(=O)[C@H](CCC(=O)O)NC(=O)CNC(=O)[C@H](CC(=O)O)NC(=O)[C@H](Cc1ccccc1)NC(=O)CC1C(=O)c2cccc3c(N4CCCCC4)ccc(c23)C1=O)C(=O)O]

In Experimental Examples 210, 220, 230, 240, 250, 260, 270 and 280, the above water-soluble peptide fluorescence material is respectively placed in environments having a pH value of 10, 9, 8, 7, 6, 5, 4 and 3 for testing. In Experimental Examples 210 to 230, the water-soluble peptide fluorescence material is respectively placed in environments having the pH value of 10, 9 and 8. As shown in FIG. 2, Experimental Examples 210 to 230 have low fluorescence intensities, so no significant fluorescence marker is shown. Even through the fluorescence intensity of Experimental Example 240 is slightly increased in a neutral environment (pH=7), but the fluorescence intensity thereof is still similar to Experimental Examples 210 to 230, so no significant fluorescence is shown. In addition, the water-soluble peptide fluorescence material of Experimental Example 250 in acidic environment (pH=6), but the fluorescence intensity thereof has no significant change compared to Experimental Examples 210 to 240.

While the pH value is decreased to 5 (Experimental Example 260), the fluorescence intensity of the water-soluble peptide fluorescence material is significantly increased to about 350 fluorescent units, and the emission peak is at about 550 nm to show the green fluorescence as observed in FIG. 1B. Then, the pH value is decreased to 4, and the fluorescence intensity of Experimental Example 270 is increased to about 500 fluorescent units. In Experimental Example 280, the pH value is decreased to 3, and the fluorescence intensity thereof is significantly increased to about 900 fluorescent units. It is worth noting that, the best known fluorescence material has a maximum fluorescence intensity of only about 350 fluorescent units in the acidic environment. Relatively, the water-soluble peptide fluorescence material provided by the present disclosure is able to achieve a fluorescence intensity of 900 fluorescent units, which not only provides obvious marker, but also achieves the same effect of the fluorescence at a low concentration, and thereby reduces the costs. In addition, the fluorescence intensity of Experimental Example 240 (pH=3) is 25.5 times of the fluorescence intensity of Experimental Example 280 (pH=7), which represents that the water-soluble peptide fluorescence material has obvious light-emitting interval and easily to identify and detect positions of the acidic cells.

Figure 3:
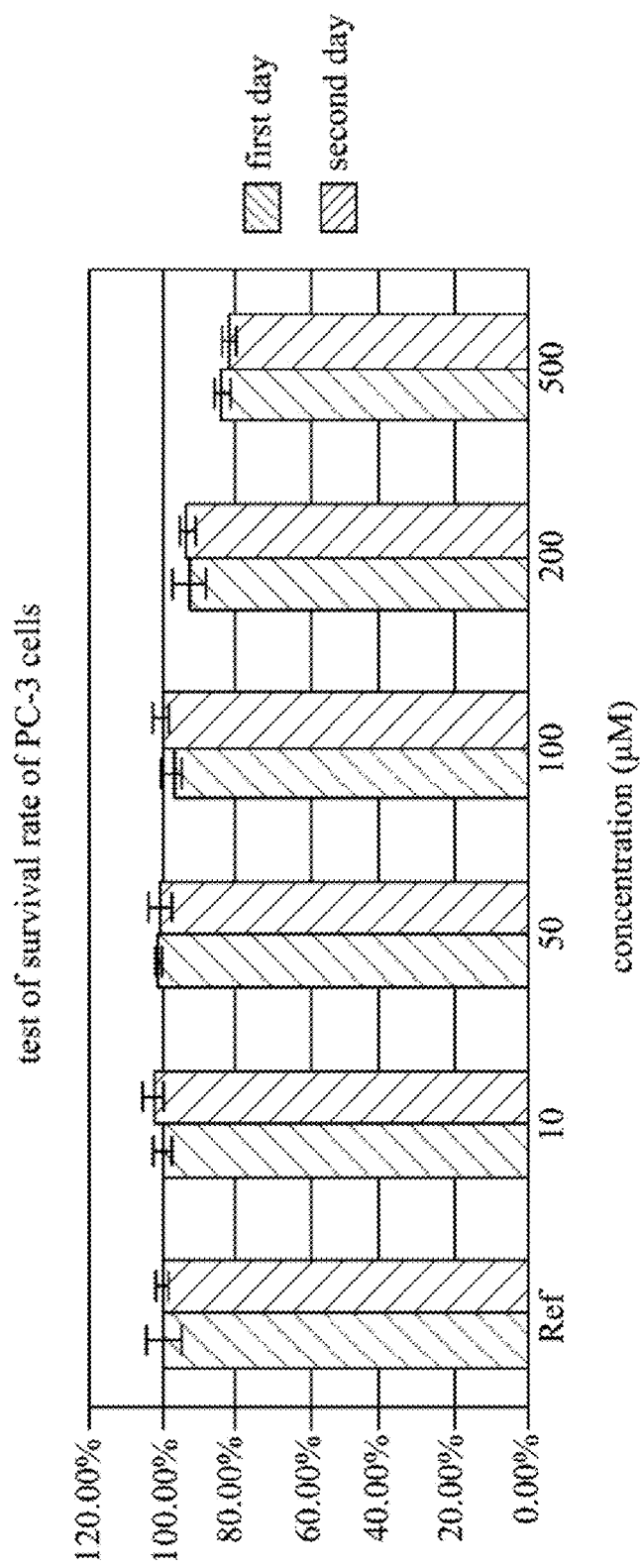
FIG. 3 illustrates survival rate of PC-3 cells in different concentrations of the water-soluble peptide fluorescence material.

Continuing in FIG. 3, which illustrates survival rate of PC-3 cell in different concentrations of the water-soluble peptide fluorescence material. The water-soluble peptide fluorescence material has a structure of following formula including a peptide sequence Phe-Asp-Gly-Glu-Ala (SEQ ID NO: 5):

As shown in FIG. 3, the PC-3 cell (BCRC-60122, Food Industry Research and Development Institute, FIRDI) has a survival rate of 80% after placing in the water-soluble peptide fluorescence material of 500 μM for two days. The above experimental result is much better than a standard of IC50 (50% inhibitory concentration). IC50 represents a concentration of a drug that is required for 50% survival rate of the cells, which means that a certain concentration of a drug is used to detect a cell mortality rate of 50%, and the certain concentration is also referred as 50% inhibitory concentration. Described in different ways, when a ratio of death cells to original cells is 50%, the corresponding concentration is 50% inhibitory concentration. The water-soluble peptide fluorescence material of the present disclosure has low toxicity and excellent compatibility to PC-3 cells, so as to avoid mass mortality of the cells. In addition, HeLa, MCF-7, CTXTAN2, PC12, WSI, 3T3L1 cells are also tested. The water-soluble peptide fluorescence material has excellent compatibility with these cells since the survival rate of these cell are all over 50%.

The water-soluble peptide fluorescence material is prepared by a solid phase peptide synthesis (SPPS), which includes following steps:

1. A first amino acid monomer is grafted to a resin, and an amino group of the first amino acid monomer having a first protective group thereon.
2. The first protective group is removed from the amino group.
3. A coupling agent is used to make

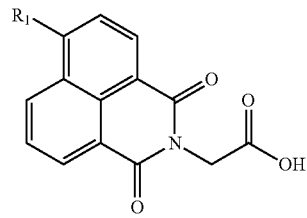

couple with the amino group (protective group thereon is removed) of the first amino acid monomer to form the water-soluble peptide fluorescence material, and $R_1$ is independently selected from hydrogen or a nitrogen-containing functional group.

4. The water-soluble peptide fluorescence material is cleaved from the resin.

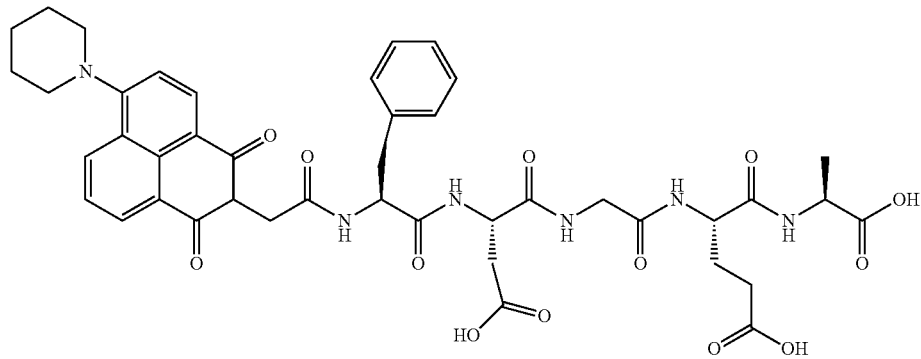 [SMILES: C[C@H](NC(=O)[C@H](CCC(=O)O)NC(=O)CNC(=O)[C@H](CC(=O)O)NC(=O)[C@H](Cc1ccccc1)NC(=O)CC1C(=O)c2cccc3c(N4CCCCC4)ccc(c23)C1=O)C(=O)O]

In some embodiments, the nitrogen-containing functional group is glucosamine, nitro group, pyrrolidine, piperidine, azepane or azocane.

It is worth noting that a second amino acid monomer the same with or different from the first amino acid monomer is coupled to the amino group of the first amino acid monomer after step 2. The second amino acid monomer has a second protective group, which is removed to expose an amino group of the second amino acid monomer. Then

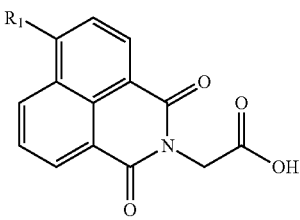

is coupled to the amino group of the second amino acid monomer. As such, amino acid amino acid sequence of the water-soluble peptide fluorescence material could be controlled to develop color at different pH value. Following is embodiments to further describe a method of preparing the water-soluble peptide fluorescence material.

1. Synthesis of Terminal Luminophore

First, a terminal luminophore of the water-soluble peptide fluorescence material is synthesized by adding acid anhydride, glycine and triethylamine in an ethanol solvent to prepare a mixture, which is refluxed for 6 hours, and the above reaction is traced by thin-layer chromatography (TLC). After the reaction, the mixture is cooled to a room temperature, and most of the ethanol solvent is removed by a rotational vacuum concentrator. Then, a hydrochloric acid having a molar concentration of 1M is slowly added to precipitate a solid. After a suction filtration process, the solid is took out and purified by recrystallization, and a solid product is obtained by filtering. Various reactants of the terminal luminophore and the products obtained from these reactants are listed in Table 1.

TABLE 1

Synthesis of various terminal luminophores by different acid anhydrides.

| acid anhydride (weight, mol) | glycine (weight, mol) | triethylamine (volume, mol) | abbreviation of the product (color, weight, yield) |
|---|---|---|---|
| 1,8-Naphthalic anhydride (1.5 g, 7.58 mmol) | glycine (1.7 g, 22.67 mmol) | triethylamine (3.2 ml, 22.8 mmol) | NI foumula(IV-1) (white, 1.3278 g, 68.65%) |
| 4-piperidine-1,8-naphthalimide (2.142 g, 7.6 mmol) | glycine (1.710 g, 22.8 mmol) | triethylamine (3.19 mol, 22.8 mmol) | PPNI foumula (IV-2) (yellow, 1.60 g, 66%) |
| 4-pyrrolidino-1,8-naphthalimide (1.335 g, 5 mmol) | glycine (1.125 g, 15 mmol) | triethylamine (2.1 ml, 15 mmol) | PRNI foumula (IV-3) (orange, 0.21 g, 13%) |
| 4-azepanyl-1,8-naphthalimide (0.407 g, 1.38 mmol) | glycine (0.517 g, 6.9 mmol) | triethylamine (0.97 ml, 6.9 mmol) | AHNI foumula (IV-4) (yellow, 0.462 g, 91%) |

TABLE 1-continued

Synthesis of various terminal luminophores by different acid anhydrides.

| acid anhydride (weight, mol) | glycine (weight, mol) | triethylamine (volume, mol) | abbreviation of the product (color, weight, yield) |
|---|---|---|---|
| 4-azocanylacetic-1,8-naphthalimide (0.428 g, 1.38 mmol) | glycine (0.517 g, 6.9 mmol) | triethylamine (0.97 ml, 6.9 mmol) | AONI (IV-5) (yellow, 0.460 g, 91%) |

NI has a structure of formula (IV-1):

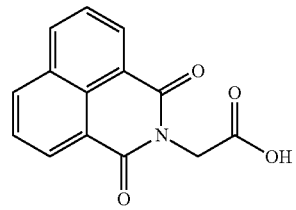

The product of formula (IV-1) is under structure analysis by an nuclear magnetic resonance ($^1$H NMR), and the NMR spectroscopy is shown below:

$^1$H NMR (300 MHz, DMSO-d6) δ=4.78 (s, 2H; CH$_2$), 7.94 (dd, J(H, H)=7.8, 7.8 Hz, 2H; CH), 8.55 (d, J(H, H)=7.8 Hz, 2H; CH), 8.56 (d, J(H, H)=7.8 Hz, 2H; CH). The structure of formula (IV-1) is referred to NI (1,8-naphthalimide-N-acetic acid) in order to facilitate the subsequent descriptions.

PPNI has a structure of formula (IV-2):

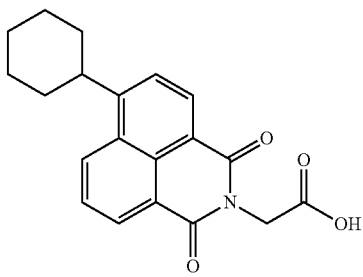

The product of formula (IV-2) is under structure analysis by the nuclear magnetic resonance ($^1$H NMR), and the NMR spectroscopy is shown below:

$^1$H NMR (300 MHz, DMSO-d6): δ=1.68-1.75 (br, 2H; CH$_2$), 1.80-1.95 (br, 4H; CH$_2$), 3.26 (t, J=5.0 Hz, 4H; CH$_2$), 4.75 (s, 2H; CH$_2$), 7.36 (d, J=8.1 Hz, 1H; CH), 7.87 (dd, J=7.5, 7.5 Hz, 1H; CH), 8.44 (d, J=8.1 Hz, 1H; CH), 8.51 (d, J=7.5 Hz, 1H; CH), 8.54 (d, J=7.5 Hz, 1H; CH). The structure of formula (IV-2) is referred to PPNI (4-piperidinyl-naphthalimide) in order to facilitate the subsequent descriptions.

PRNI has a structure of formula (IV-3):

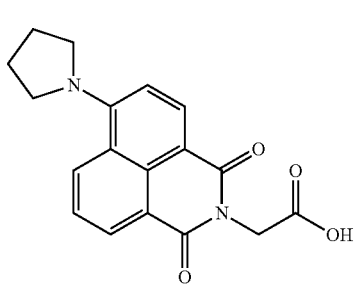

(IV-3)

The product of formula (IV-3) is under structure analysis by an nuclear magnetic resonance ($^1$H NMR and $^{13}$C NMR), and the NMR spectroscopy is shown below:

$^1$H NMR (300 MHz, DMSO-d6): δ=2.05 (s, 4H; CH$_2$), 3.79 (s, 4H; CH$_2$), 4.71 (s, 2H; CH$_2$), 6.87 (d, J=8.7 Hz, 1H; CH), 7.63 (dd, J=7.6, 7.6 Hz, 1H; CH), 8.23 (d, J=8.7 Hz, 1H; CH), 8.44 (d, J=7.6 Hz, 1H; CH), 8.76 (d, J=7.6 Hz, 1H; CH);

$^{13}$C NMR (75 MHz, DMSO-d6): δ=26.5, 41.8, 53.9, 109.0, 109.4, 121.9, 122.6, 124.1, 131.7, 131.8, 134.1, 150.1, 153.3, 163.3, 164.5, 170.6;

MS [ESI$^-$]: m/z (%): expected value: 324.11, experimental value: 323.1 [M-H]$^-$. The structure of formula (IV-3) is referred to PRNI (4-pyrrolidyl-naphthalimide) in order to facilitate the subsequent descriptions.

AHNI has a structure of formula (IV-4):

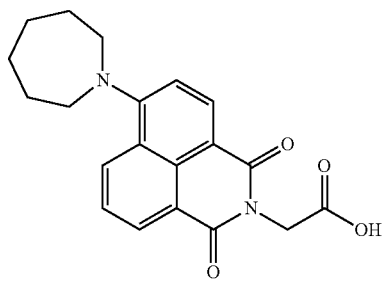

(IV-4)

The product of formula (IV-4) is under structure analysis by an nuclear magnetic resonance ($^1$H NMR and $^{13}$C NMR), and the NMR spectroscopy is shown below:

$^1$H NMR (300 MHz, DMSO-d6): δ=1.60-1.80 (br, 4H; CH$_2$), 1.80-2.05 (br, 4H; CH$_2$), 3.61 (t, J=5.25 Hz, 4H; CH), 4.71 (s, 2H; CH$_2$), 7.19 (d, J=8.4 Hz, 1H; CH), 7.70 (dd, J=7.8, 7.8 Hz, 1H; CH), 8.26 (d, J=8.4 Hz, 1H; CH), 8.42 (d, J=7.8 Hz, 1H; CH), 8.47 (d, J=7.8 Hz, 1H; CH);

$^{13}$C NMR (75 MHz, DMSO-d6): δ=28.2, 28.7, 41.8, 55.6, 112.3, 113.8, 122.5, 124.9, 125.3, 131.0, 131.7, 133.2, 133.4, 157.9, 163.4, 164.3, 170.5;

MS [ESI$^-$]: m/z (%): expected value: 352.14, experimental value: 350.9 [M-H]$^-$. The structure of formula (IV-4) is referred to AHNI (4-azacycloheptyl-naphthalimide) in order to facilitate the subsequent descriptions.

AONI has a structure of formula (IV-5):

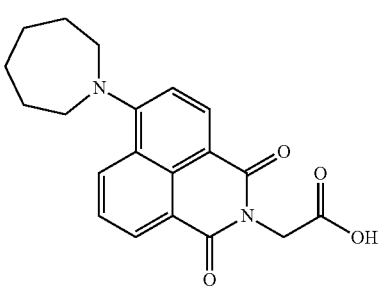

(IV-5)

The product of formula (IV-5) is under structure analysis by an nuclear magnetic resonance ($^1$H NMR and $^{13}$C NMR), and the NMR spectroscopy is shown below:

$^1$H NMR (300 MHz, DMSO-d6): δ=1.55-1.75 (br, 6H; CH$_2$), 1.75-1.95 (br, 4H; CH$_2$), 3.68 (t, J=10.5 Hz, 4H; CH), 4.72 (s, 2H; CH$_2$), 7.26 (d, J=8.7 Hz, 1H; CH), 7.71 (dd, J=8.0, 8.0 Hz, 1H; CH), 8.27 (d, J=8.7 Hz, 1H; CH), 8.4 (d, J=8.0 Hz, 1H; CH), 8.54 (d, J=8.0 Hz, 1H; CH);

$^{13}$C NMR (75 MHz, DMSO-d6): δ=25.3, 27.7, 27.8, 41.8, 54.8, 111.6, 113.3, 122.6, 124.5, 125.1, 131.3, 131.8, 132.7, 133.6, 156.4, 163.3, 164.4, 170.6;

MS [ESI$^-$]: m/z (%): expected value: 366.16, experimental value: 365.0 [M-H]$^-$. The structure of formula (IV-5) is referred to AONI (4-azacyclooctyl-naphthalimide) in order to facilitate the subsequent descriptions.

2-1. Solid Phase Peptide Synthesis (Grafting One Amino Acid)

After the synthesis of the terminal luminophore, a solid phase peptide synthesis (SPPS) is applied to prepare the water-soluble peptide fluorescence material using 2-chlorotrityl chloride resin, amino acid and the terminal luminophore.

The amino acid is grafted to the terminal luminophore by following steps. The 2-chlorotrityl chloride resin (1.2 g, 1 mmol) is swelled in anhydrous dichloromethane (CH$_2$Cl$_2$) for 30 min, and a first amino acid having a Fmoc protective group is dissolved in anhydrous N, N-dimethylformamide (DMF) and N, N-diisopropylethylamine (DIEA, 0.83 ml, 5.0 mmol). Then, the first amino acid is reacted with the 2-chlorotrityl chloride resin for 1 hour to graft the first amino acid on the 2-chlorotrityl chloride resin.

After that, piperidine (20% in DMF) is added and reacted for 35 minutes to remove the Fmoc protective group on the first amino acid, and the above step is repeated twice (2 minutes each time). Subsequently, the terminal luminophore, DIEA (0.83 ml, 5.0 mmol) and O-(benzotriazol-1-yl)-N,N,N'',N''-tetramethyluraniumhexafluorophosphate (HBTU, 0.76 g, 2.0 mmol) are dissolved in anhydrous DMF and reacted with the 2-chlorotrityl chloride resin. During the reaction, the HBTU acts as a coupling agent to make the terminal luminophore couple to a free amino group (the Fmoc protective group thereon is removed) of the first amino acid.

The reaction mixture is stirred overnight, and then the water-soluble peptide fluorescence material is cleaved from the 2-chlorotrityl chloride resin through treatment of trifluoroacetic acid (90% in deionized water) for 3 hours. The resulting solution is further dried under a stream of air, and diethyl ether is added to precipitate a target product. Then, the precipitate is dried under vacuum to remove residual solvent, and the remained solid product is the water-soluble peptide fluorescence material. Continuing in Table 2, which shows different water-soluble peptide fluorescence materials synthesized from various amino acids and terminal luminophores.

TABLE 2

Different water-soluble peptide fluorescence materials synthesized from various amino acids and terminal luminophores.

| Embodiment | first amino acid (weight, mol) | terminal luminophore (weight, mol) | structure of the product (color, weight) |
|---|---|---|---|
| Embodiment 1 | Fmoc-L-phenylalanine (0.78 g, 2.0 mmol) | NI (0.51 g, 2 mmol) | III-1 (white solid, 0.14 g) |
| Embodiment 2 | Fmoc-O-tert-butyl-L-tyrosine (0.92 g, 2.0 mmol) | NI (0.77 g, 3 mmol) | III-2 (white solid, 0.14 g) |
| Embodiment 3 | Fmoc-L-glycine (0.59 g, 2.0 mmol) | NI (0.77 g, 3 mmol) | III-3 (white solid, 0.17 g) |
| Embodiment 4 | Fmoc-L-phenylalanine (0.78 g, 2.0 mmol) | PPNI (1.02 g, 3 mmol) | III-4 (white solid, 0.18 g) |

The product of Embodiment 1 has a structure of formula (III-1):

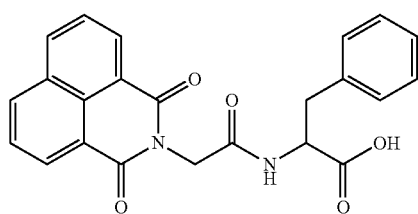

(III-1)

The NMR spectroscopy of the product in Embodiment 1 is shown below:

$^1$H NMR (300 MHz, DMSO-d6): δ=2.90-3.15 (m, 2H, CH$_2$), 4.40-4.50 (m, 1H, CH), 4.73 (s, 2H, CH$_2$), 7.20-7.40 (m, 5H, CH), 7.94 (t, 2H, CH), 8.50-8.60 (m, 4H, CH), 8.63 (d, 1H, NH);

$^{13}$C NMR (75 MHz, DMSO-d6): δ=38.1, 43.1, 54.9, 122.9, 127.3, 128.2, 128.4, 129.1, 130.2, 131.8, 132.3, 135.5, 135.7, 138.6, 164.1, 167.4;

MS [ESI$^-$]: m/z (%): expected value: 402.12, experimental value: 401.0 [M-H]$^-$.

Figure 4:
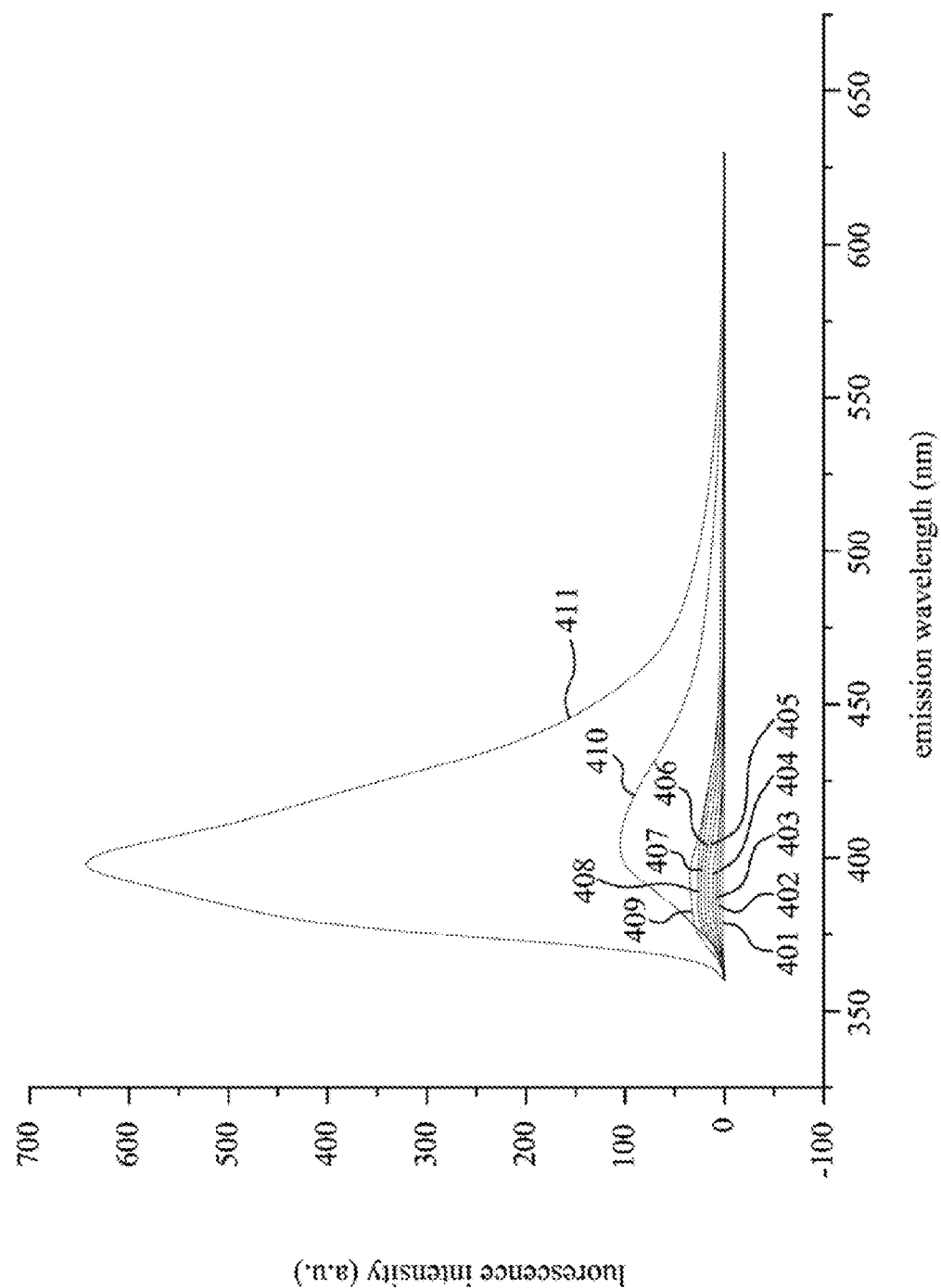
FIG. 4 illustrates a fluorescence intensity and an emission wavelength of the water-soluble peptide fluorescence material of formula (III-1) in co-solvents having different proportions of water and dimethyl sulfoxide.

Continuing in FIG. 4, which illustrates a fluorescence intensity and an emission wavelength of the water-soluble peptide fluorescence material of formula (III-1) in co-solvents having different proportions of water and dimethyl sulfoxide. In Experimental Example 401, 402, 403, 404, 405, 406, 407, 408, 409, 410 and 411, water respectively has 0, 10, 20, 30, 40, 50, 60, 70, 80, 90 and 100% of a total volume of the co-solvent. As shown in FIG. 4, the water-soluble peptide fluorescence material of formula (III-1) has low fluorescence intensity in co-solvents of Experimental Example 401 to 408. As such, no significant fluorescence marker is shown, so it is difficult to observe apparent fluorescence visually. While a volume ratio of water is increased to 80% (Experimental Example 409) and 90% (Experimental Example 410), the fluorescence intensity is significantly increased to 50 and 100 fluorescent units, and weak fluorescence could be observed. The volume ratio of water is further increased to 100%, and the fluorescence intensity of Experimental Example 411 is sharply increased to about 650 fluorescent units, so as to provide a more obvious fluorescence marker. Given the above, the fluorescence intensity of the water-soluble peptide fluorescence material of formula (III-1) is increased corresponding to the increase of the volume ratio of water, which is also referred as aggregation-induced emission (AIE). In addition, the water-soluble peptide fluorescence material of formula (III-1) has the emission wavelength of about 400 nm, so the observed fluorescence has a color of blue violet.

The product of Embodiment 2 has a structure of formula (III-2):

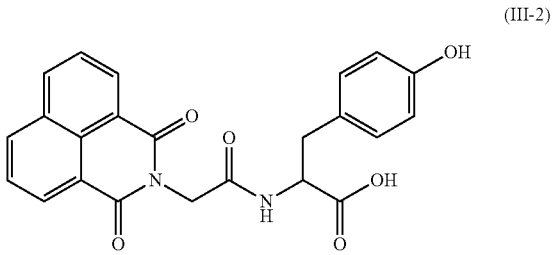 [SMILES: O=C(CN1C(=O)c2cccc3cccc(c23)C1=O)NC(Cc1ccc(O)cc1)C(=O)O]

(III-2)

The NMR spectroscopy of the product in Embodiment 2 is shown below:

$^1$H NMR (300 MHz, DMSO-d6): δ=2.75-3.10 (m, 2H, CH$_2$), 4.30-4.45 (m, 1H, CH), 4.73 (s, 1H, CH$_2$), 6.72 (d, J=7.8 Hz, 2H, CH), 7.06 (d, J=7.8 Hz, 2H, CH), 7.92 (t, J=7.65 Hz, 2H, CH), 8.40-8.70 (m, 5H, CH, NH), 9.10-9.40 (br, 1H, OH);

$^{13}$C NMR (75 MHz, DMSO-d6): δ=37.1, 43.0, 55.0, 116.0, 122.8, 128.2, 128.3, 128.4, 131.1, 131.8, 132.3, 135.5, 156.9, 164.1, 167.5, 173.8;

MS [ESI$^-$]: m/z (%): expected value: 418.12, experimental value: 417.1 [M-H]$^-$.

The product of Embodiment 3 has a structure of formula (III-3):

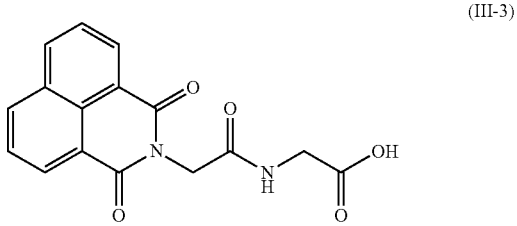 [SMILES: O=C(O)CNC(=O)CN1C(=O)c2cccc3cccc(c23)C1=O]

(III-3)

The NMR spectroscopy of the product in Embodiment 3 is shown below:

$^1$H NMR (300 MHz, DMSO-d6): δ=3.83 (d, J=5.7 Hz, 2H, CH$_2$), 4.76 (s, 2H, CH$_2$), 7.94 (t, J=10.4 Hz, 2H, CH), 8.50-8.65 (m, 5H, CH, NH);

$^{13}$C NMR (75 MHz, DMSO-d6): δ=41.6, 43.1, 122.9, 128.2, 128.5, 131.8, 132.3, 135.5, 164.2, 168.0, 172.0;

MS [ESI$^-$]: m/z (%): expected value: 312.07, experimental value: 310.90 [M-H]$^-$.

The product of Embodiment 4 has a structure of formula (III-4):

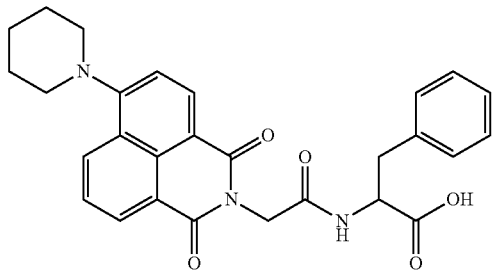

(III-3)

The NMR spectroscopy of the product in Embodiment 3 is shown below:

$^1$H NMR (300 MHz, DMSO-d6): δ=1.60-1.80 (m, 2H; CH$_2$), 1.80-1.95 (m, 4H; CH$_2$), 2.90-3.15 (m, 2H; CH$_2$), 3.15-3.30 (m, 4H; CH$_2$), 4.40-4.55 (m, 1H; CH), 4.699 (s, 2H; CH$_2$), 7.20-7.40 (m, 5H; CH), 7.84 (t, J=7.95 Hz, 1H; CH), 8.35-8.55 (m, 3H; CH), 8.61 (d, J=7.8 Hz, 1H; CH);

$^{13}$C NMR (75 MHz, DMSO-d6): δ=24.8, 26.6, 37.8, 42.8, 54.6, 54.9, 115.8, 115.9, 123.3, 126.4, 126.8, 127.4, 129.1, 130.16, 130.24, 131.6, 131.7, 133.3, 138.3, 157.8, 163.7, 164.3, 167.7, 173.6;

MS [ESI$^-$]: m/z (%): expected value: 485.53, experimental value: 484.1 [M-H]$^-$.

2-2. Solid Phase Peptide Synthesis (Grafting Two Amino Acids)

Embodiments of grafting two amino acids is begun with swelling 2-chlorotrityl chloride resin (1.2 g, 1 mmol) in anhydrous dichloromethane (CH$_2$Cl$_2$) for 30 min, and a first amino acid having a Fmoc protective group is dissolved in anhydrous DMF and DIEA (0.83 ml, 5.0 mmol). Then, the first amino acid is reacted with the 2-chlorotrityl chloride resin for 1 hour to graft the first amino acid on the 2-chlorotrityl chloride resin. After that, piperidine (20% in DMF) is added and reacted for 35 minutes to remove the Fmoc protective group on the first amino acid, and the above step is repeated twice (2 minutes each time). Subsequently, a second amino acid having a Fmoc protective group, DIEA (0.83 ml, 5.0 mmol) and HBTU (0.76 g, 2.0 mmol) are dissolved in anhydrous DMF and reacted with the 2-chlorotrityl chloride resin. During the reaction, the HBTU acts as a coupling agent to make the second amino acid couple to a free amino group (the Fmoc protective group thereon is removed) of the first amino acid.

Then, piperidine (20% in DMF) is again added and reacted for 20 minutes, and the above step is repeated twice (2 minutes each time) to remove Fmoc protective group on the second amino acid. Subsequently, the terminal luminophore, DIEA (0.83 ml, 5.0 mmol) and HBTU (0.76 g, 2.0 mmol) are dissolved in anhydrous DMF and reacted with the 2-chlorotrityl chloride resin. During the reaction, the HBTU acts as the coupling agent to make the terminal luminophore couple to a free amino group (the Fmoc protective group thereon is removed) of the second amino acid.

The reaction mixture is stirred overnight, and then the water-soluble peptide fluorescence material is cleaved from the 2-chlorotrityl chloride resin through treatment of trifluoroacetic acid (90% in deionized water) for 3 hours. The resulting solution is further dried under a stream of air, and diethyl ether is added to precipitate a target product. Then, the precipitate is dried under vacuum to remove residual solvent, and the remained solid product is the water-soluble peptide fluorescence material, which is under structure analysis by a nuclear magnetic resonance ($^1$H NMR and $^{13}$C NMR). Continuing in Table 3, which shows different water-soluble peptide fluorescence materials synthesized from two amino acids and various terminal luminophores.

TABLE 3

Different water-soluble peptide fluorescence materials synthesized from two amino acids and various terminal luminophores.

| Embodiment | first amino acid (weight, mol) | second amino acid (weight, mol) | terminal luminophore (weight, mol) | structure of the product (color, weight) |
|---|---|---|---|---|
| Embodiment 5 | Fmoc-L-glycine (0.59 g, 2.0 mmol) | Fmoc-L-glycine (0.59 g, 2.0 mmol) | NI (0.51 g, 2.0 mmol) | III-5 (white solid, 0.35 g) |
| Embodiment 6 | Fmoc-L-phenylalanine (1.16 g, 3.0 mmol) | Fmoc-L-phenylalanine (1.55 g, 4.0 mmol) | NI (1.53 g, 6.0 mmol) | III-6 (white solid, 0.35 g) |
| Embodiment 7 | Fmoc-L-phenylalanine (1.16 g, 3.0 mmol)) | Fmoc-L-tyrosine (1.84 g, 4.0 mmol) | NI (1.53 g, 6.0 mmol) | III-7 (white solid, 1.06 g) |
| Embodiment 8 | Fmoc-L-tyrosine (1.38 g, 3.0 mmol)) | Fmoc-L-phenylalanine (1.55 g, 4.0 mmol) | NI (1.53 g, 6.0 mmol) | III-8 (white solid, 1.15 g) |

TABLE 3-continued

Different water-soluble peptide fluorescence materials synthesized from two amino acids and various terminal luminophores.

| Embodiment | first amino acid (weight, mol) | second amino acid (weight, mol) | terminal luminophore (weight, mol) | structure of the product (color, weight) |
|---|---|---|---|---|
| Embodiment 9 | Fmoc-L-tyrosine (0.919 g, 2.0 mmol)) | Fmoc-L-tyrosine (0.919 g, 2.0 mmol) | NI (0.51 g, 2.0 mmol) | III-9 (pale yellow solid, 0.32 g) |
| Embodiment 10 | Fmoc-L-phenylalanine (1.16 g, 3.0 mmol) | Fmoc-L-glycine (1.19 g, 4.0 mmol) | NI (1.53 g, 6.0 mmol) | III-10 (white solid, 0.48 g) |
| Embodiment 11 | Fmoc-L-glycine (0.89 g, 3.0 mmol) | Fmoc-L-phenylalanine (1.55 g, 4.0 mmol) | NI (1.53 g, 6.0 mmol) | III-11 (white solid, 0.38 g) |
| Embodiment 12 | Fmoc-L-glycine (0.4 g, 1.3 mmol) | Fmoc-O-tert-butyl-L-tyrosine (0.61 g, 1.3 mmol) | NI (0.35 g, 1.3 mmol) | III-12 (white solid, 0.22 g) |
| Embodiment 13 | Fmoc-O-tert-butyl-L-tyrosine (0.92 g, 2.0 mmol) | Fmoc-L-glycine (0.6 g, 2.0 mmol) | NI (0.77 g, 3.0 mmol) | III-13 (white solid, 0.18 g) |
| Embodiment 14 | Fmoc-L-phenylalanine (0.58 g, 1.5 mmol) | Fmoc-L-phenylalanine (0.58 g, 1.5 mmol) | PPNI (0.51 g, 1.5 mmol) | III-14 (yellow solid, 0.515 g) |
| Embodiment 15 | Fmoc-L-phenylalanine (0.58 g, 1.5 mmol) | Fmoc-L-tyrosine (0.69 g, 1.5 mmol) | PPNI (0.51 g, 1.5 mmol) | III-15 (yellow solid, 0.534 g) |
| Embodiment 16 | Fmoc-L-aspartic acid (0.62 g, 1.5 mmol) | Fmoc-L-aspartic acid (0.62 g, 1.5 mmol) | PPNI (0.677 g, 2.0 mmol) | III-16 (dark brown solid, 0.376 g) |
| Embodiment 17 | Fmoc-L-aspartic acid (0.62 g, 1.5 mmol) | Fmoc-L-phenylalanine (0.58 g, 1.5 mmol) | PPNI (0.677 g, 2.0 mmol) | III-17 (yellow solid, 0.554 g) |
| Embodiment 18 | Fmoc-L-phenylalanine (0.58 g, 1.5 mmol) | Fmoc-L-phenylalanine (0.58 g, 1.5 mmol) | PRNI (0.486 g, 1.5 mmol) | III-18 (orange solid, 0.434 g) |
| Embodiment 19 | Fmoc-L-phenylalanine (0.58 g, 1.5 mmol) | Fmoc-L-phenylalanine (0.58 g, 1.5 mmol) | AHNI (0.528 g, 1.5 mmol) | III-19 (yellow solid, 0.611 g) |
| Embodiment 20 | Fmoc-L-phenylalanine (0.29 g, 0.75 mmol) | Fmoc-L-phenylalanine (0.29 g, 0.75 mmol) | AONI (0.366 g, 1 mmol) | III-20 (yellow solid, 0.248 g) |
| Embodiment 21 | Fmoc-L-glutamic acid (0.425 g, 1.0 mmol) | Fmoc-L-phenylalanine (0.387 g, 1.0 mmol) | PPNI (0.507 g, 1.50 mmol) | III-21 (yellow solid, 0.230 g) |

The product of Embodiment 5 has a structure of formula (III-5):

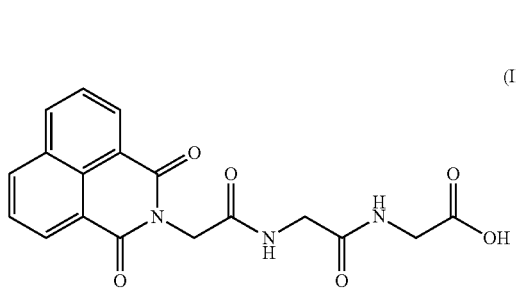

(III-5)

The NMR spectroscopy of the product in Embodiment 5 is shown below:

$^1$H NMR (300 MHz, DMSO-d6): δ=3.75-3.85 (m, 4H; CH$_2$), 4.783 (s, 1H; CH$_2$), 7.94 (t, J=7.8 Hz, 2H; CH), 8.24 (t, J=5.7 Hz, 1H; NH), 8.50-8.65 (m, 5H; CH, NH);

$^{13}$C NMR (75 MHz, DMSO-d6): δ=41.5, 42.7, 43.3, 122.9, 128.3, 131.8, 135.5, 164.3, 168.1, 170.0, 172.1;

MS [ESI$^-$]: m/z (%): expected value: 369.10, experimental value: 367.9 [M-H]$^-$.

The product of Embodiment 6 has a structure of formula (III-6):

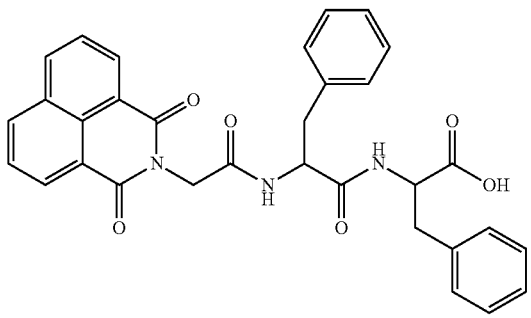

(III-6)

The NMR spectroscopy of the product in Embodiment 6 is shown below:

$^1$H NMR (300 MHz, DMSO-d6): δ=2.75-3.15 (m, 4H; CH$_2$), 4.40-4.50 (m, 1H; CH), 4.55-4.65 (m, 1H; CH), 4.688 (s, 2H; CH$_2$), 7.20-7.35 (m, 10H; CH), 7.90-8.00 (t, J=7.8 Hz, 2H; CH), 8.38 (d, J=8.1 Hz, 1H; NH), 8.48 (d, J=8.4 Hz, 1H; NH), 8.54 (d, J=7.5 Hz, 4H; CH);

$^{13}$C NMR (75 MHz, DMSO-d6): δ=37.7, 38.5, 43.1, 54.6, 122.8, 127.1, 127.4, 128.2, 128.4, 128.9, 129.1, 130.0, 130.2, 131.8, 132.3, 135.4, 138.3, 138.5, 164.1, 167.3, 171.8, 173.6;

MS [ESI$^-$]: m/z (%): expected value: 549.19, experimental value: 548.1 [M-H]$^-$.

The product of Embodiment 7 has a structure of formula (III-7):

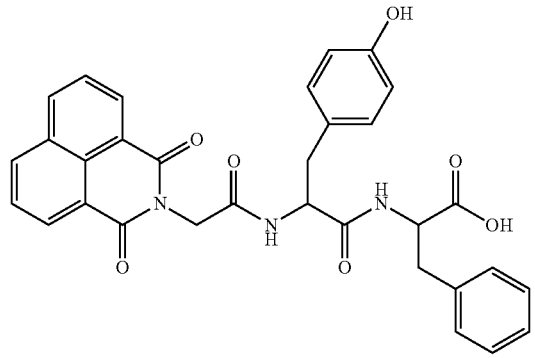

(III-7)

The NMR spectroscopy of the product in Embodiment 7 is shown below:

$^1$H NMR (300 MHz, DMSO-d6): δ=2.60-3.15 (m, 4H; CH$_2$), 4.40-4.55 (m, 2H; CH), 4.693 (s, 2H; CH$_2$), 6.68 (d, J=8.1 Hz, 2H; CH), 7.06 (d, J=8.4 Hz, 2H; CH), 7.15-7.40 (m, 5H; CH), 7.3 (t, J=7.65 Hz, 2H; CH), 8.33 (d, J=7.5 Hz, 1H; NH), 8.42 (d, J=8.4 Hz, 1H; NH), 8.53 (d, J=8.1 Hz, 4H; CH);

$^{13}$C NMR (75 MHz, DMSO-d6): δ=37.7, 43.1, 54.5, 55.0, 115.8, 122.9, 127.4, 128.2, 128.4, 128.6, 129.2, 130.1, 131.1, 131.8, 132.3, 135.5, 138.4, 156.7, 164.1, 167.3, 171.9, 173.6;

MS [ESI$^-$]: m/z (%): expected value: 565.18, experimental value: 564.22 [M-H]$^-$.

The product of Embodiment 8 has a structure of formula (III-8):

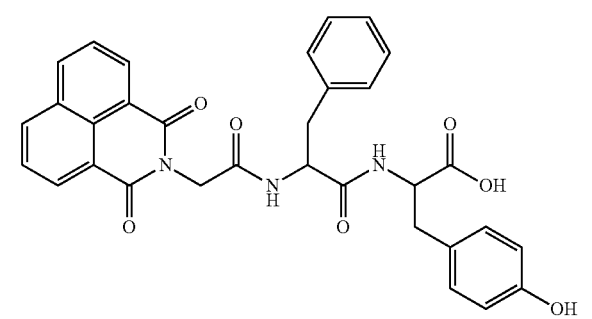

(III-8)

The NMR spectroscopy of the product in Embodiment 8 is shown below:

$^1$H NMR (300 MHz, DMSO-d6): δ=2.75-3.10 (m, 4H; CH$_2$), 4.35-4.45 (m, 1H; CH), 4.55-4.65 (m, 1H; CH), 4.694 (s, 2H; CH$_2$), 6.70 (d, J=8.4 Hz, 2H; CH), 7.06 (d, J=8.4 Hz, 2H; CH), 7.20-7.35 (m, 5H; CH), 7.92 (t, J=7.65 Hz, 2H; CH), 8.29 (d, J=7.5 Hz, 1H; NH), 8.45-8.55 (m, 5H; CH, NH);

$^{13}$C NMR (75 MHz, DMSO-d6): δ=40.0, 38.5, 43.1, 54.6, 54.9, 116.0, 122.8, 127.1, 128.2, 128.3, 128.4, 128.9, 130.2, 131.0, 131.8, 132.3, 135.5, 138.6, 156.9, 164.1, 167.4, 171.8, 173.7;

MS [ESI$^-$]: m/z (%): expected value: 565.18, experimental value: 564.2 [M-H]$^-$.

The product of Embodiment 9 has a structure of formula (III-9):

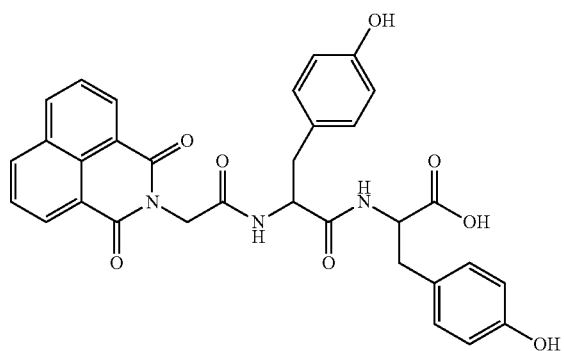

(III-9)

The NMR spectroscopy of the product in Embodiment 9 is shown below:

$^1$H NMR (300 MHz, DMSO-d6): δ=2.60-3.15 (m, 4H; CH$_2$), 4.30-4.40 (m, 1H; CH), 4.40-4.55 (m, 1H; CH), 2.70-2.90 (m, 1H; CH$_2$), 4.697 (s, 2H; CH$_2$), 6.60-6.75 (m, 4H; CH), 7.00-7.15 (m, 4H; CH), 7.94 (t, J=7.8 Hz, 2H; CH), 8.21 (d, J=6.9 Hz, 1H; NH), 8.43 (d, J=8.4 Hz, 1H; NH), 8.54 (d, J=7.8 Hz, 4H; CH);

$^{13}$C NMR (75 MHz, DMSO-d6): δ=37.0, 37.7, 43.2, 55.0, 115.8, 116.0, 122.9, 128.2, 128.4, 128.7, 131.0, 131.2, 131.8, 132.3, 135.5, 156.7, 156.9, 164.2, 167.3, 171.9, 173.8;

MS [ESI$^-$]: m/z (%): expected value: 581.1, experimental value: 580.5 [M-H]$^-$.

The product of Embodiment 10 has a structure of formula (III-10):

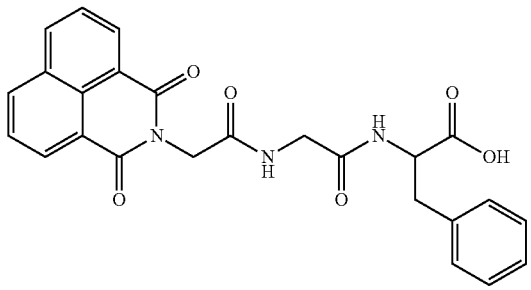

(III-10)

The NMR spectroscopy of the product in Embodiment 10 is shown below:

$^1$H NMR (300 MHz, DMSO-d6): δ=2.85-3.00 (m, 1H; CH$_2$), 3.00-3.15 (m, 1H; CH$_2$), 3.65-3.90 (m, 2H; CH$_2$), 4.35-4.55 (m, 1H; CH), 4.70-4.80 (m, 2H; CH$_2$), 7.20-7.35 (m, 5H; CH), 7.94 (t, J=7.65 Hz, 1H; CH), 8.20 (d, J=8.4 Hz, 1H; NH), 8.50-8.60 (m, 5H; CH, NH);

$^{13}$C NMR (75 MHz, DMSO-d6): δ=37.9, 43.3, 54.5, 122.9, 127.4, 128.2, 128.5, 129.2, 130.1, 131.8, 132.3, 135.5, 138.4, 164.3, 168.0, 169.5, 173.7;

MS [ESI$^-$]: m/z (%): expected value: 459.14, experimental value: 458.4 [M-H]$^-$.

Figure 5:
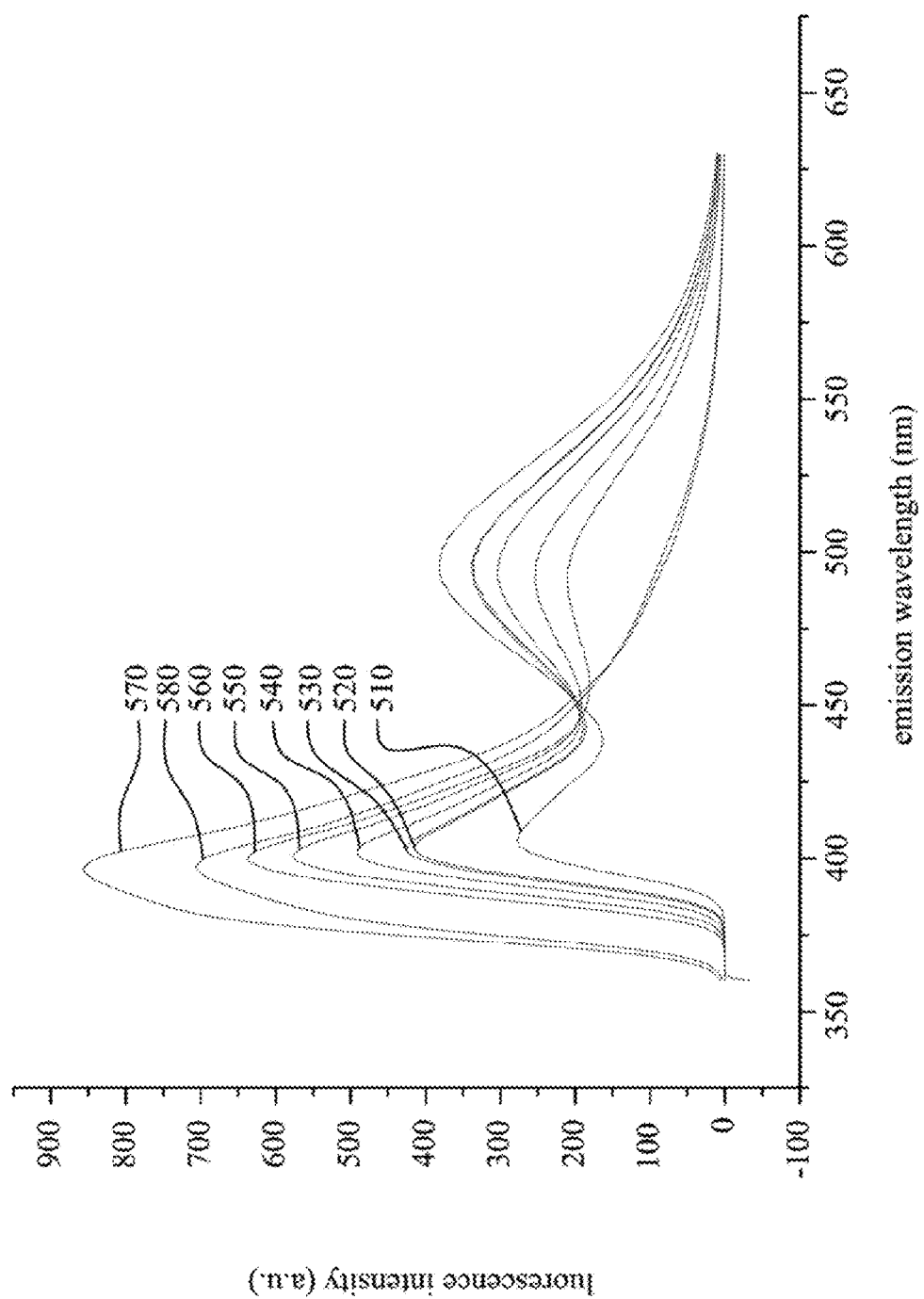
FIG. 5 illustrates a fluorescence intensity and an emission wavelength of the water-soluble peptide fluorescence material of formula (III-10) at different pH values.

Continuing in FIG. 5, which illustrates a fluorescence intensity and an emission wavelength of the water-soluble peptide fluorescence material of formula (III-10) at different pH values. In Experimental Examples 510, 520, 530, 540, 550, 560, 570 and 580, the water-soluble peptide fluorescence material of formula (III-10) is respectively placed in environments having a pH value of 10, 9, 8, 7, 6, 5, 4 and 3 for testing. In Experimental Examples 510 to 560, the water-soluble peptide fluorescence material is placed in environments having the pH value of 10 to 5, and two emission peaks are shown in FIG. 5. One emission peak is at about 400 nm, and the other emission peak is at about 500 nm, so the observed fluorescence is mixed light of green light and purple light. Then, the pH value is further decrease to 4 (Experimental Example 570) and 3 (Experimental Example 580), and only the emission peak at about 400 nm is remained, so the observed fluorescence has a color of purple in Experimental Examples 570 and 580. Therefore, the water-soluble peptide fluorescence material of formula (III-10) is able to detect and mark locations of acidic cells by change of the color.

The product of Embodiment 11 has a structure of formula (III-11):

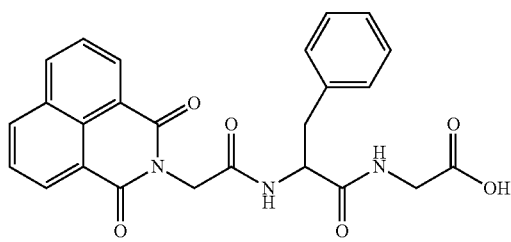

(III-11)

The NMR spectroscopy of the product in Embodiment 11 is shown below:

$^1$H NMR (300 MHz, DMSO-d6): δ=2.75-2.90 (m, 1H; CH$_2$), 3.00-3.10 (m, 1H; CH$_2$), 3.80-3.90 (m, 2H; CH$_2$), 4.50-4.65 (m, 1H; CH), 4.65-4.75 (m, 2H; CH$_2$), 7.20-7.35 (m, 5H; CH), 7.94 (t, J=7.8 Hz, 2H; CH), 8.46 (t, J=5.85 Hz, 1H; NH), 8.54 (d, J=7.8 Hz, 4H; CH), 8.60 (d, J=8.1 Hz, 1H; NH);

$^{13}$C NMR (75 MHz, DMSO-d6): δ=38.8, 41.6, 43.1, 54.8, 122.8, 127.2, 128.2, 128.3, 129.0, 130.2, 131.8, 132.2, 135.4, 138.7, 164.1, 167.5, 172.0, 172.3;

MS [ESI$^-$]: m/z (%): expected value: 459.14, experimental value: 458.1 [M-H]$^-$.

The product of Embodiment 12 has a structure of formula (III-12):

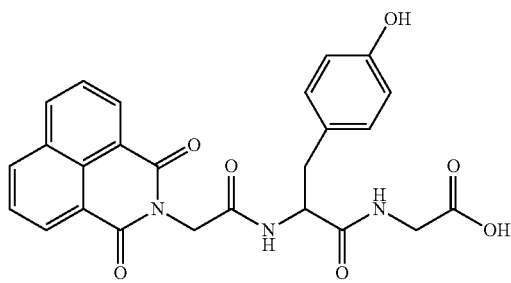

(III-12)

The NMR spectroscopy of the product in Embodiment 12 is shown below:

$^1$H NMR (300 MHz, DMSO-d6): δ=2.65-2.80 (m, 1H; CH$_2$), 2.90-3.00 (m, 1H; CH$_2$), 3.75-3.85 (m, 2H; CH$_2$), 4.40-4.55 (m, 1H; CH$_2$), 4.713 (s, 2H; CH$_2$), 6.69 (d, J=8.1

Hz, 2H; CH), 7.08 (d, J=8.1 Hz, 2H; CH), 7.92 (t, J=7.8 Hz, 2H; CH), 8.4 (d, J=5.4 Hz, 1H; NH), 8.52 (d, J=7.2 Hz, 4H; CH);

$^{13}$C NMR (75 MHz, DMSO-d6): δ=38.0, 43.2, 55.2, 115.8, 122.9, 128.2, 128.4, 128.7, 131.1, 131.8, 132.3, 135.5, 156.7, 164.2, 167.4, 172.1, 172.4;

MS [ESI$^-$]: m/z (%): expected value: 475.14, experimental value: 474.0 [M-H]$^-$.

The product of Embodiment 13 has a structure of formula (III-13):

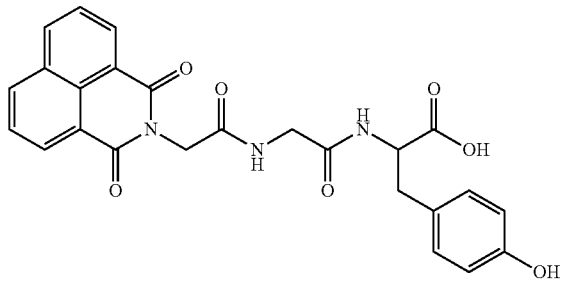

(III-13)

The NMR spectroscopy of the product in Embodiment 13 is shown below:

$^1$H NMR (300 MHz, DMSO-d6): δ=2.75-2.85 (m, 1H; CH$_2$), 2.90-3.05 (m, 1H; CH$_2$), 3.65-3.90 (m, 2H; CH$_2$), 4.30-4.45 (m, 1H; CH), 4.76 (d, J=3.0 Hz, 2H; CH$_2$), 6.68 (d, J=8.1 Hz, 2H; CH), 7.04 (d, J=8.4 Hz, 2H; CH), 7.94 (t, J=7.8 Hz, 2H; CH), 8.10 (d, J=7.8 Hz, 1H; NH), 8.50-8.65 (m, 4H; CH);

$^{13}$C NMR (75 MHz, DMSO-d6): δ=37.1, 42.6, 43.3, 54.8, 116.0, 122.9, 128.2, 128.3, 128.36, 128.43, 131.0, 131.8, 132.0, 132.3, 135.5, 135.8, 156.9, 164.0, 164.3, 168.0, 169.4, 170.3, 173.8;

MS [ESI$^-$]: m/z (%): expected value: 475.14, experimental value: 474.0 [M-H]$^-$.

The product of Embodiment 14 has a structure of formula (III-14):

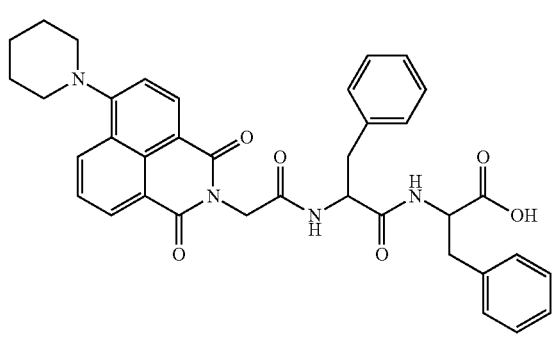

(III-14)

The NMR spectroscopy of the product in Embodiment 14 is shown below:

$^1$H NMR (300 MHz, DMSO-d6): δ=1.60-1.80 (br, 2H; CH$_2$), 1.80-1.95 (br, 4H; CH$_2$), 2.70-3.20 (m, 4H; CH$_2$), 3.23 (s, 4H; CH$_2$), 4.40-4.55 (m, 1H; CH), 4.55-4.75 (m, 2H; CH, CH$_2$), 7.15-7.45 (m, 11H; CH), 7.82 (dd, J=6.9, 6.9 Hz, 1H; CH), 8.35-8.60 (m, 5H; CH, NH);

$^{13}$C NMR (75 MHz, DMSO-d6): δ=24.8, 26.7, 37.7, 38.5, 43.0, 46.2, 54.5, 54.9, 111.5, 115.75, 115.85, 123.3, 126.4, 126.8, 127.2, 127.4, 128.9, 129.2, 130.1, 130.3, 131.6, 133.3, 138.3, 138.6, 157.8, 163.7, 164.3, 167.5, 171.9, 173.6;

MS [ESI$^-$]: m/z (%): expected value: 632.26, experimental value: 631.1 [M-H]$^-$.

Figure 6:
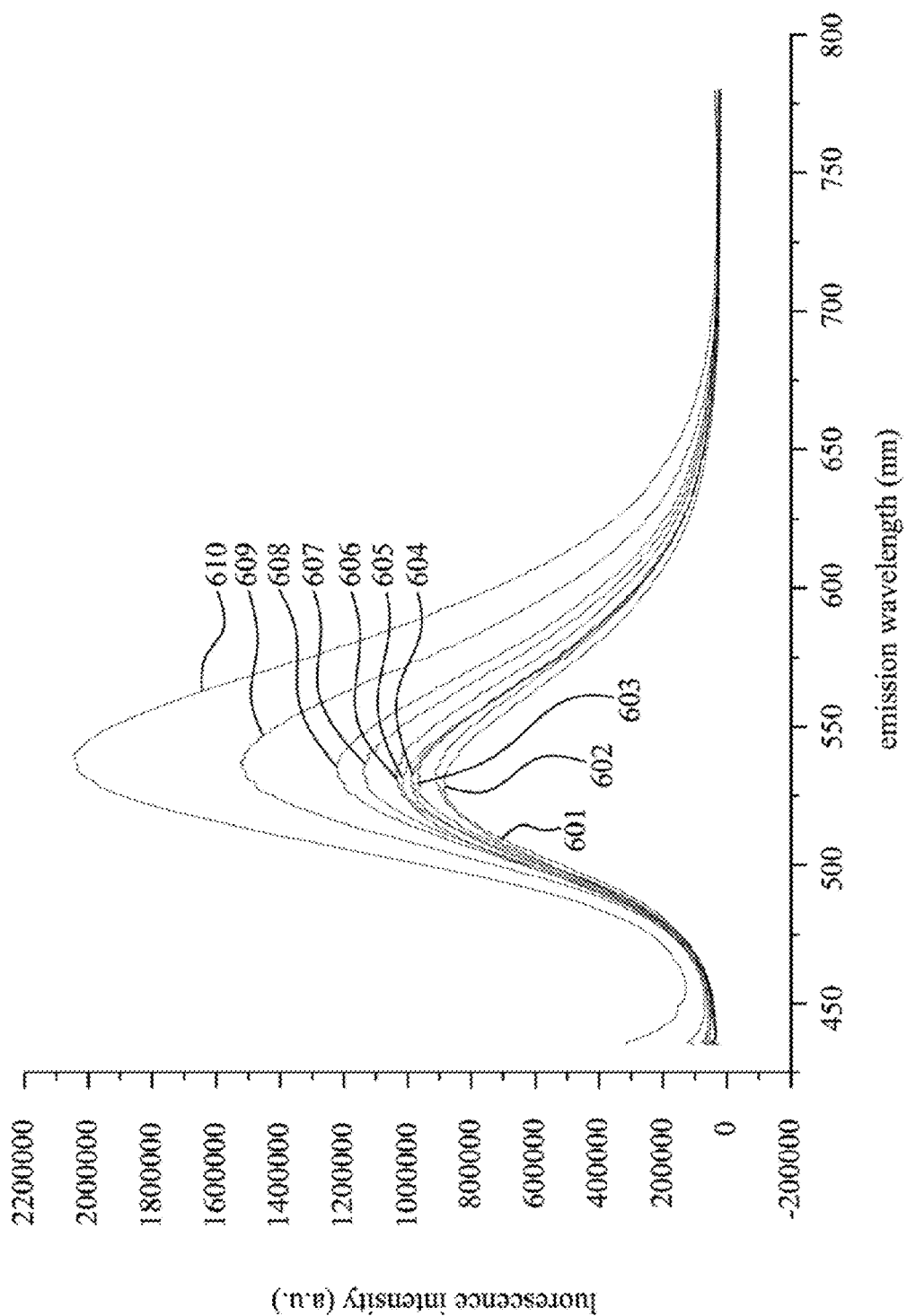
FIG. 6 illustrates a fluorescence intensity and an emission wavelength of the water-soluble peptide fluorescence material of formula (III-14) in co-solvents having different proportions of glycerol and methanol.

Continuing in FIG. 6, which illustrates a fluorescence intensity and an emission wavelength of the water-soluble peptide fluorescence material of formula (III-14) in co-solvents having different proportions of glycerol and methanol. In Experimental Example 601, 602, 603, 604, 605, 606, 607, 608, 609 and 610, methanol respectively has 0, 10, 20, 30, 40, 50, 60, 70, 80 and 90% of a total volume of the co-solvent. As shown in FIG. 6, the water-soluble peptide fluorescence material of formula (III-14) has largest fluorescence intensity in Experimental Example 610, so as to provide a more obvious fluorescence marker. Given the above, the fluorescence intensity of the water-soluble peptide fluorescence material of formula (III-14) is increased corresponding to the increase of the volume ratio of methanol, so the water-soluble peptide fluorescence material of formula (III-14) also has a phenomenon of aggregation-induced emission (AIE) in methanol. In addition, the water-soluble peptide fluorescence material of formula (III-14) has the emission wavelength of about 550 nm, so the observed fluorescence has a color of green.

The product of Embodiment 15 has a structure of formula (III-15):

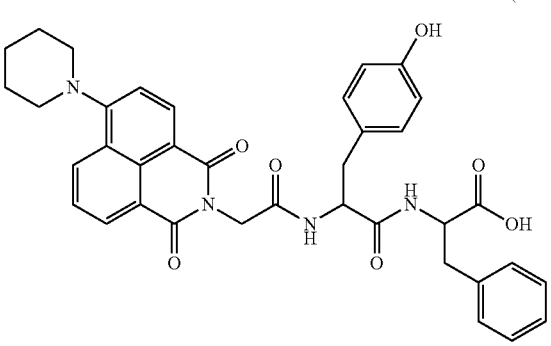

(III-15)

The NMR spectroscopy of the product in Embodiment 15 is shown below:

$^1$H NMR (300 MHz, DMSO-d6): δ=1.65-1.80 (br, 2H; CH$_2$), 1.80-2.00 (br, 4H; CH$_2$), 2.60-3.15 (m, 4H; CH$_2$), 3.20-3.30 (br, 4H; CH$_2$), 4.40-4.60 (m, 2H; CH), 4.66 (s, 2H; CH$_2$), 6.67 (d, J=8.4 Hz, 2H; CH), 7.06 (d, J=8.4 Hz, 2H; CH), 7.15-7.35 (m, 5H; CH), 7.37 (d, J=8.1, 1H; CH), 7.86 (dd, J=7.5, 8.4, 1H; CH), 8.30-8.55 (m, 5H; CH, NH), 9.20 (s, 1H; OH);

$^{13}$C NMR (75 MHz, DMSO-d6): δ=23.9, 25.7, 36.8, 42.0, 53.6, 54.0, 105.6, 114.8, 115.0, 122.4, 125.5, 125.9, 126.4, 127.7, 128.2, 129.1, 129.3, 130.2, 130.7, 132.4, 137.4, 155.7, 156.9, 162.8, 163.4, 166.5, 171.0, 172.7;

MS [ESI$^-$]: m/z (%): expected value: 648.26, experimental value: 647.1 [M-H]$^-$.

The product of Embodiment 16 has a structure of formula (III-16):

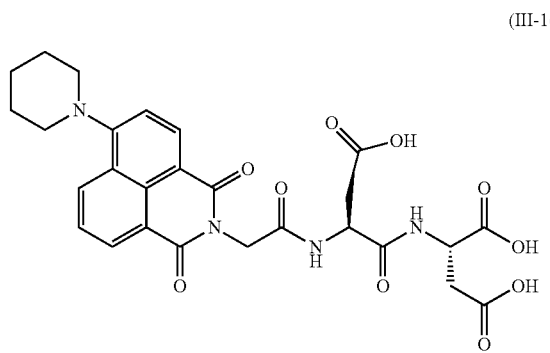

(III-16)

The NMR spectroscopy of the product in Embodiment 16 is shown below:

$^1$H NMR (300 MHz, DMSO-d6): δ=1.65-1.75 (br, 2H; CH$_2$), 1.80-1.95 (br, 4H; CH$_2$), 2.60-2.80 (m, Hz, 4H; CH$_2$), 3.20-3.35 (br, 4H; CH$_2$), 4.55-4.65 (m, 1H; CH), 4.65-4.75 (m, 3H; CH$_2$), 7.37 (d, J=8.1 Hz 1H; CH), 7.86 (t, J=7.8 Hz, 1H; CH), 8.11 (d, J=8.1 Hz, 1H; NH), 8.42 (d, J=8.1 Hz, 1H; CH), 8.49 (t, J=8.4 Hz, 2H; CH), 8.62 (d, J=7.8 Hz, 1H; NH);

$^{13}$C NMR (75 MHz, DMSO-d6): δ=23.9, 25.8, 36.0, 36.4, 42.2, 48.7, 49.4, 54.0, 114.8, 114.9, 122.4, 125.5, 125.8, 129.4, 130.8, 130.9, 132.5, 157.0, 163.0, 163.5, 167.1, 170.4, 171.6, 171.7, 172.2;

MS [ESI$^-$]: m/z (%): expected value: 568.18, experimental value: 567.0 [M-H]$^-$.

The product of Embodiment 17 has a structure of formula (III-17):

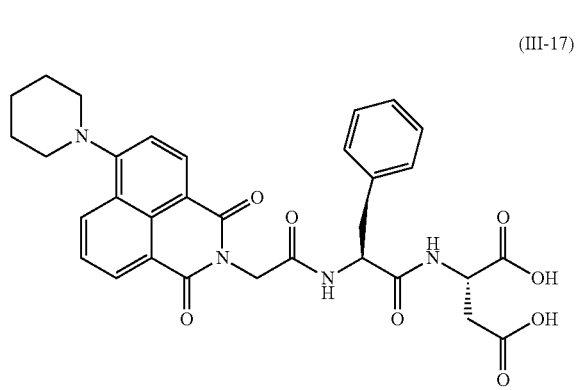 [SMILES: O=C(O)C[C@H](NC(=O)[C@H](Cc1ccccc1)NC(=O)CN1C(=O)c2cccc3c(N4CCCCC4)ccc(c23)C1=O)C(=O)O]

(III-17)

The NMR spectroscopy of the product in Embodiment 17 is shown below:

$^1$H NMR (300 MHz, DMSO-d6): δ=1.65-1.75 (br, 2H; CH$_2$), 1.80-1.90 (br, 4H; CH$_2$), 2.55-3.10 (m, 4H; CH$_2$), 3.20-3.30 (br, 4H; CH$_2$), 4.55-4.65 (m, 2H; CH), 4.67 (s, 2H; CH$_2$), 7.20-7.25 (m, 1H; CH), 7.25-7.35 (m, J=6.0 Hz, 4H; CH), 7.36 (d, J=8.1 Hz, 1H; CH), 7.86 (t, J=7.95 Hz, 1H; CH), 8.41 (d, J=8.4 Hz, 1H; CH), 8.48 (t, J=7.2 Hz, 4H; CH);

$^{13}$C NMR (75 MHz, DMSO-d6): δ=23.9, 25.7, 36.0, 37.8, 42.0, 48.7, 53.7, 54.0, 114.8, 114.9, 122.4, 125.5, 125.9, 126.3, 128.0, 129.3, 129.4, 130.7, 130.8, 132.4, 137.6, 156.9, 162.8, 163.4, 166.6, 170.9, 171.6, 172.3;

MS [ESI$^-$]: m/z (%): expected value: 600.22, experimental value: 599.0 [M-H]$^-$.

The product of Embodiment 18 has a structure of formula (III-18):

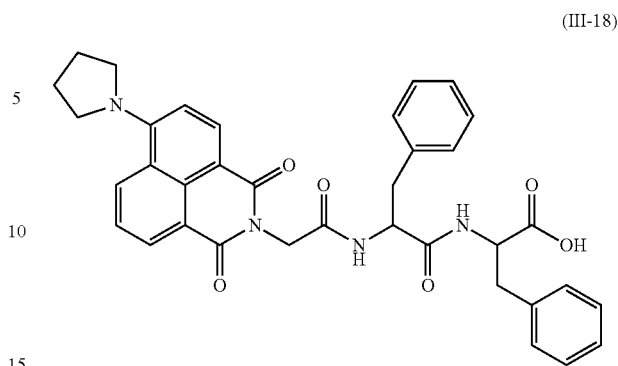

(III-18)

The NMR spectroscopy of the product in Embodiment 18 is shown below:

$^1$H NMR (300 MHz, DMSO-d6): δ=1.95-2.10 (br, 4H; CH$_2$), 2.75-3.20 (m, 4H; CH$_2$), 3.70-3.90 (br, 4H; CH$_2$), 4.40-4.55 (m, 1H; CH), 4.55-4.80 (m, 3H; CH, CH$_2$), 6.89 (d, J=7.8 Hz, 1H; CH), 7.15-7.45 (m, 10H; CH), 7.63 (dd, J=8.0, 8.0 Hz, 1H; CH), 8.23 (d, J=8.0 Hz, 1H; CH), 8.35-8.50 (m, 4H; CH, NH), 8.76 (d, J=8.0 Hz, 1H; CH);

$^{13}$C NMR (75 MHz, DMSO-d6): δ=26.5, 37.7, 38.5, 42.8, 53.8, 54.6, 109.4, 109.5, 122.3, 122.7, 124.1, 127.2, 127.4, 129.0, 129.2, 130.1, 130.3, 131.6, 133.7, 133.9, 138.3, 138.6, 151.4, 153.2, 163.5, 164.6, 167.8, 171.9, 173.6;

MS [ESI$^-$]: m/z (%): expected value: 618.25, experimental value: 617.1 [M-H]$^-$.

The product of Embodiment 19 has a structure of formula (III-19):

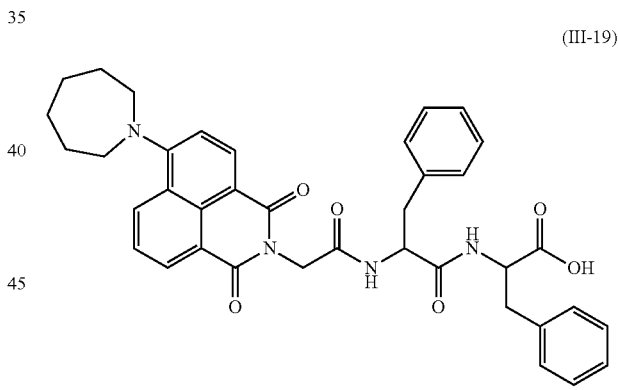

(III-19)

The NMR spectroscopy of the product in Embodiment 19 is shown below:

$^1$H NMR (300 MHz, DMSO-d6): δ=1.65-1.80 (br, 4H; CH$_2$), 1.80-2.00 (br, 4H; CH$_2$), 2.70-3.20 (m, 4H; CH$_2$), 3.60-3.75 (br, 4H; CH), 4.40-4.55 (m, 1H; CH), 4.55-4.65 (br, 1H; CH), 4.66 (s, 2H; CH$_2$), 7.20-7.40 (m, 11H; CH), 7.77 (dd, J=7.5, 8.4 Hz, 1H; CH), 8.30-8.50 (m, 4H; NH, CH), 8.56 (d, J=8.4 Hz, 1H; CH);

$^{13}$C NMR (75 MHz, DMSO-d6): δ=27.1, 28.2, 28.7, 37.7, 38.5, 54.5, 55.7, 58.8, 106.5, 113.0, 114.0, 123.0, 125.1, 127.2, 127.4, 128.9, 129.2, 130.1, 130.3, 131.6, 133.3, 138.3, 138.6, 157.9, 161.8, 163.6, 164.5, 167.6, 167.8, 171.9, 173.6;

MS [ESI$^-$]: m/z (%): expected value: 646.28, experimental value: 645.1 [M-H]$^-$.

The product of Embodiment 20 has a structure of formula (III-20):

(III-20)

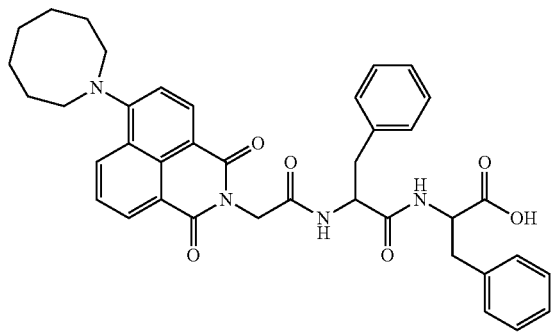

The NMR spectroscopy of the product in Embodiment 20 is shown below:

$^1$H NMR (300 MHz, DMSO-d6): δ=1.60-1.80 (br, 6H; CH$_2$), 1.80-2.00 (br, 4H; CH$_2$), 2.70-3.20 (m, 4H; CH$_2$), 3.74 (s, 4H; CH), 4.40-4.50 (m, 1H; CH), 4.50-4.70 (m, 3H; CH, CH$_2$), 7.15-7.45 (m, 11H; CH), 7.65-7.85 (br, 1H; CH), 8.31 (d, J=8.7 Hz, 1H; CH), 8.35-8.55 (m, 3H; CH, NH), 8.61 (d, J=7.5 Hz, 1H; CH);

$^{13}$C NMR (75 MHz, DMSO-d6): δ=25.3, 27.7, 27.8, 37.7, 38.5, 42.8, 54.5, 54.8, 73.0, 112.3, 113.6, 123.1, 124.7, 125.2, 127.0, 127.2, 127.4, 128.9, 129.2, 130.1, 130.3, 131.3, 131.6, 132.4, 133.4, 138.3, 138.6, 162.8, 164.5, 167.6, 171.8, 173.6;

MS [ESI$^-$]: m/z (%): expected value: 660.29, experimental value: 659.2 [M-H]$^-$.

The product of Embodiment 21 has a structure of formula (III-21):

(III-21)

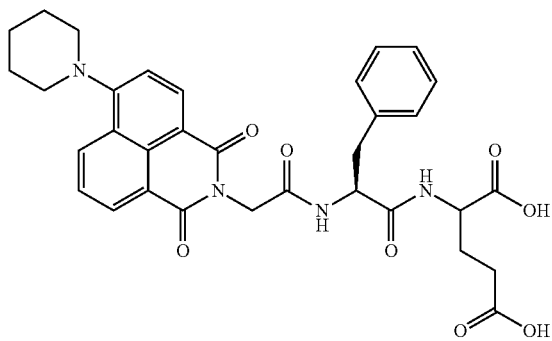

The NMR spectroscopy of the product in Embodiment 21 is shown below:

$^1$H NMR (300 MHz, DMSO-d6): δ=1.65-1.75 (br, 2H; CH$_2$), 1.80-1.90 (br, 4H; CH$_2$), 1.95-2.05 (q, J=8.6 Hz, 2H; CH$_2$), 2.25-2.35 (t, J=7.3 Hz, 2H; CH$_2$), 2.75-2.85 (m, 1H; CH$_2$), 3.05-3.15 (m, 1H; CH$_2$), 3.20-3.30 (br, 4H; CH$_2$), 4.20-4.30 (q, J=9.4 Hz, 1H; CH), 4.50-4.60 (q, J=9.8 Hz, 1H; CH), 4.60-4.70 (s, 2H; CH$_2$), 7.20-7.25 (m, 1H; CH), 7.25-7.35 (m, J=6.0 Hz, 4H; CH), 7.35 (d, J=8.1 Hz, 1H; NH), 7.85 (t, J=7.5 Hz, 1H; CH), 8.25 (d, J=7.5 Hz, 1H; NH), 8.4 (d, J=8.1 Hz, 1H; NH), 8.5 (t, J=7.2 Hz, 3H; CH);

$^{13}$C NMR (75 MHz, DMSO-d6): δ=24.3, 26.1, 26.8, 30.5, 37.8, 42.0, 42.5, 51.8, 54.2, 54.4, 115.2, 115.3, 122.8, 125.8, 126.2, 126.7, 128.5, 129.7, 131.1, 132.8, 138.2, 157.3, 163.3, 163.9, 167.2, 171.5, 173.5, 174.2;

MS [ESI$^-$]: m/z (%): expected value: 614.65, experimental value: 613.10 [M-H]$^-$.

Figure 7:
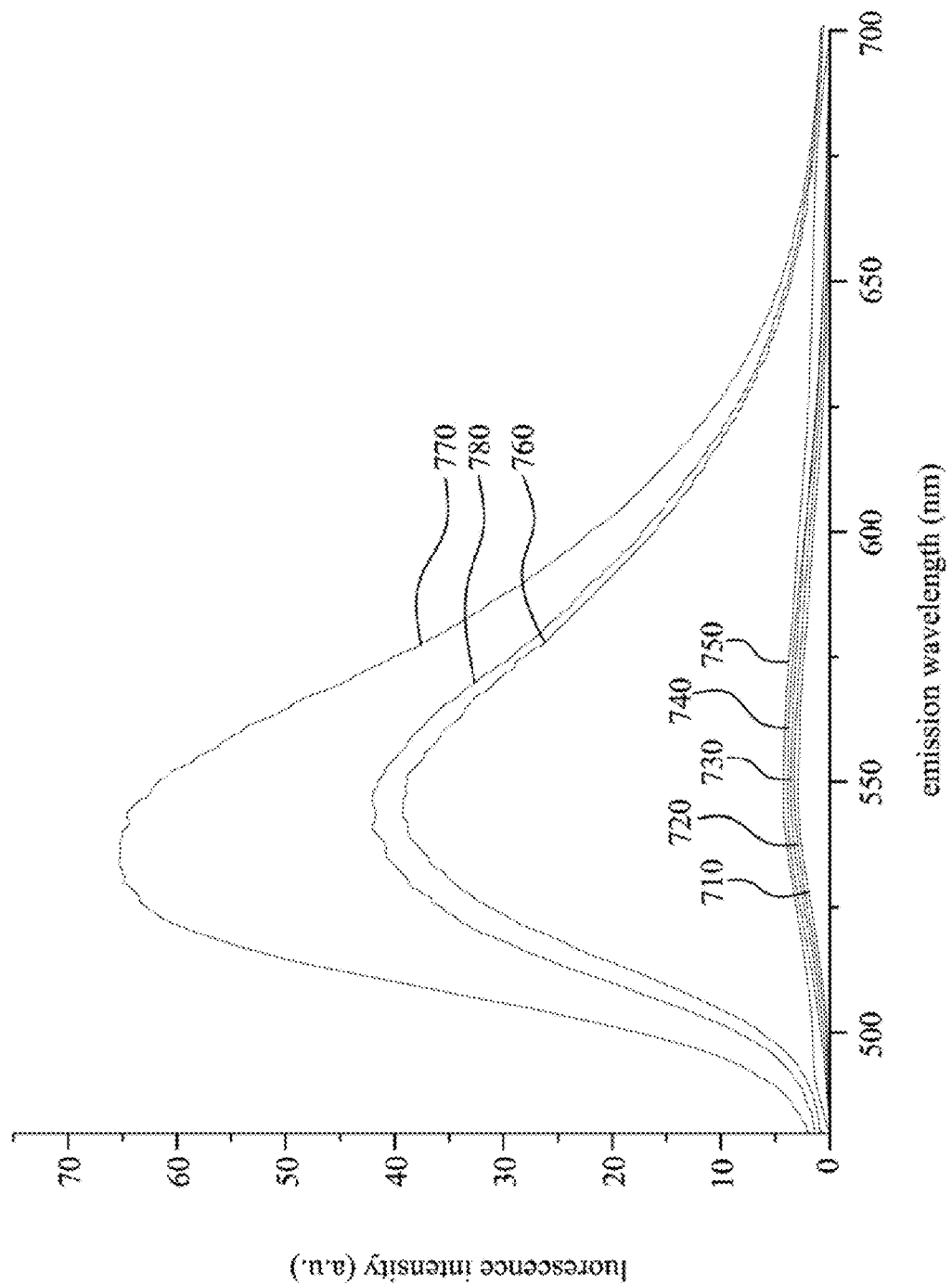
FIG. 7 illustrates a fluorescence intensity and an emission wavelength of the water-soluble peptide fluorescence material of formula (III-21) at different pH values.

Continuing in FIG. 7, which illustrates a fluorescence intensity and an emission wavelength of the water-soluble peptide fluorescence material of formula (III-21) at different pH values. In Experimental Examples 710, 720, 730, 740, 750, 760, 770 and 780, the water-soluble peptide fluorescence material of formula (III-21) is respectively placed in environments having a pH value of 10, 9, 8, 7, 6, 5, 4 and 3 for testing. In Experimental Examples 710 to 750, the water-soluble peptide fluorescence material is placed in environments having the pH value of 10 to 6. As shown in FIG. 7, Experimental Examples 710 to 750 have low fluorescence intensities, so no significant fluorescence marker is shown. While the pH value is decreased to 5 (Experimental Examples 760), the fluorescence intensity is significantly increased, and the emission peak is at about 550 nm to show the green fluorescence. The pH value is decreased to 4 in Experimental Examples 770, and the fluorescence intensity thereof is further increased. However, the fluorescence intensity of Experimental Examples 780 is decreased when the pH value is decreased from 4 to 3. Therefore, the water-soluble peptide fluorescence material of formula (III-21) has the highest fluorescence intensity at the pH value of 4.

2-3. Solid Phase Peptide Synthesis (Grafting Three Amino Acids)

Embodiments of grafting three amino acids is begun with swelling 2-chlorotrityl chloride resin (1.2 g, 1 mmol) in anhydrous dichloromethane (CH$_2$Cl$_2$) for 30 min, and a first amino acid having a Fmoc protective group is dissolved in anhydrous DMF and DIEA (0.62 ml, 3.75 mmol). Then, the first amino acid is reacted with the 2-chlorotrityl chloride resin for 30 minutes to graft the first amino acid on the 2-chlorotrityl chloride resin. After that, piperidine (20% in DMF) is added and reacted for 20 minutes to remove the Fmoc protective group on the first amino acid, and the above step is repeated twice (2 minutes each time). Subsequently, a second amino acid having a Fmoc protective group, DIEA (0.6225 ml, 3.75 mmol) and HBTU (0.57 g, 1.5 mmol) are dissolved in anhydrous DMF and reacted with the 2-chlorotrityl chloride resin. During the reaction, the HBTU acts as a coupling agent to make the second amino acid couple to a free amino group (the Fmoc protective group thereon is removed) of the first amino acid.

Then, piperidine (20% in DMF) is again added and reacted for 20 minutes, and the above step is repeated twice (2 minutes each time) to remove the Fmoc protective group on the second amino acid. Subsequently, a third amino acid having a Fmoc protective group, DIEA (0.6225 ml, 3.75 mmol) and HBTU (0.57 g, 1.5 mmol) are dissolved in anhydrous DMF and reacted with the 2-chlorotrityl chloride resin. During the reaction, the HBTU acts as the coupling agent to make the third amino acid couple to a free amino group (the Fmoc protective group thereon is removed) of the second amino acid.

In order to remove the Fmoc protective group on the third amino acid, piperidine (20% in DMF) is added and reacted for 20 minutes, and the above step is repeated twice (2 minutes each time). After that, the terminal luminophore, DIEA (0.83 ml, 5.0 mmol) and HBTU (0.76 g, 2.0 mmol) are dissolved in anhydrous DMF and reacted with the 2-chlorotrityl chloride resin. During the reaction, the HBTU acts as the coupling agent to make the terminal luminophore couple to a free amino group (the Fmoc protective group thereon is removed) of the third amino acid.

The reaction mixture is stirred overnight, and then the water-soluble peptide fluorescence material is cleaved from the 2-chlorotrityl chloride resin through treatment of trifluoroacetic acid (90% in deionized water) for 3 hours. The resulting solution is further dried under a stream of air, and diethyl ether is added to precipitate a target product. Then, the precipitate is dried under vacuum to remove residual solvent, and the remained solid product is the water-soluble peptide fluorescence material, which is under structure analysis by a nuclear magnetic resonance ($^1$H NMR and $^{13}$C NMR). Continuing in Table 3, which shows different water-soluble peptide fluorescence materials synthesized from three amino acids and various terminal luminophores.

TABLE 4

Different water-soluble peptide fluorescence materials synthesized from three amino acids and various terminal luminophores.

| Embodiment | first amino acid (weight, mol) | second amino acid (weight, mol) | third amino acid (weight, mol) | terminal luminophore (weight, mol) | structure of the product (color, weight) |
|---|---|---|---|---|---|
| Embodiment 22 | Fmoc-L-aspartic acid (0.62 g, 1.5 mmol) | Fmoc-L-aspartic acid (0.62 g, 1.5 mmol) | Fmoc-L-phenylalanine (0.58 g, 1.5 mmol) | PPNI (0.677 g, 2.0 mmol) | III-22 (orange solid, 0.554 g) |
| Embodiment 23 | Fmoc-L-glutamic acid (0.425 g, 1.0 mmol) | Fmoc-L-aspartic acid (0.414 g, 1.0 mmol) | Fmoc-L-phenylalanine (0.387 g, 1.0 mmol) | PPNI (0.4365 g, 1.0 mmol) | III-23 (yellow solid, 0.310 g) |

The product of Embodiment 22 has a structure of formula (III-22):

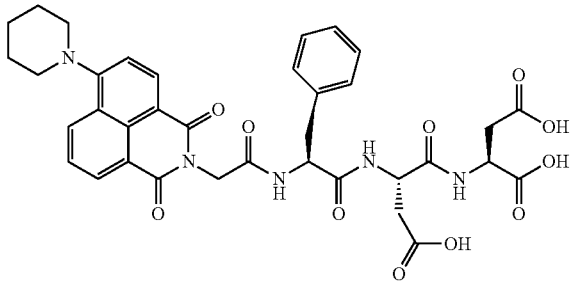

(III-22)

The NMR spectroscopy of the product in Embodiment 22 is shown below:

$^1$H NMR (300 MHz, DMSO-d6): δ=1.65-1.75 (br, 2H; CH$_2$), 1.85-1.95 (br, 4H; CH$_2$), 2.60-3.10 (m, 6H; CH$_2$), 3.20-3.30 (br, 4H; CH$_2$), 4.50-4.60 (m, 2H; CH), 4.67 (s, 3H; CH$_2$), 7.20-7.25 (m, 1H; CH), 7.25-7.35 (m, 4H; CH), 7.36 (d, J=8.1 Hz, 1H; CH), 7.85 (t, J=7.8 Hz, 1H; CH), 8.05 (d, J=8.1 Hz, 1H; NH), 8.41 (d, J=8.4 Hz, 1H; NH), 8.45-8.55 (m, 4H; CH);

$^{13}$C NMR (75 MHz, DMSO-d6): δ=23.9, 25.7, 35.9, 36.1, 37.6, 42.1, 48.6, 49.4, 53.9, 54.0, 114.8, 114.9, 122.4, 125.5, 125.8, 126.2, 128.0, 129.3, 130.7, 132.4, 137.8, 156.9, 162.8, 163.4, 166.8, 170.3, 171.1, 171.6, 171.7, 172.1, 181.0;

MS [ESI$^-$]: m/z (%): expected value: 715.25, experimental value: 714.2 [M-H]$^-$.

Figure 8:
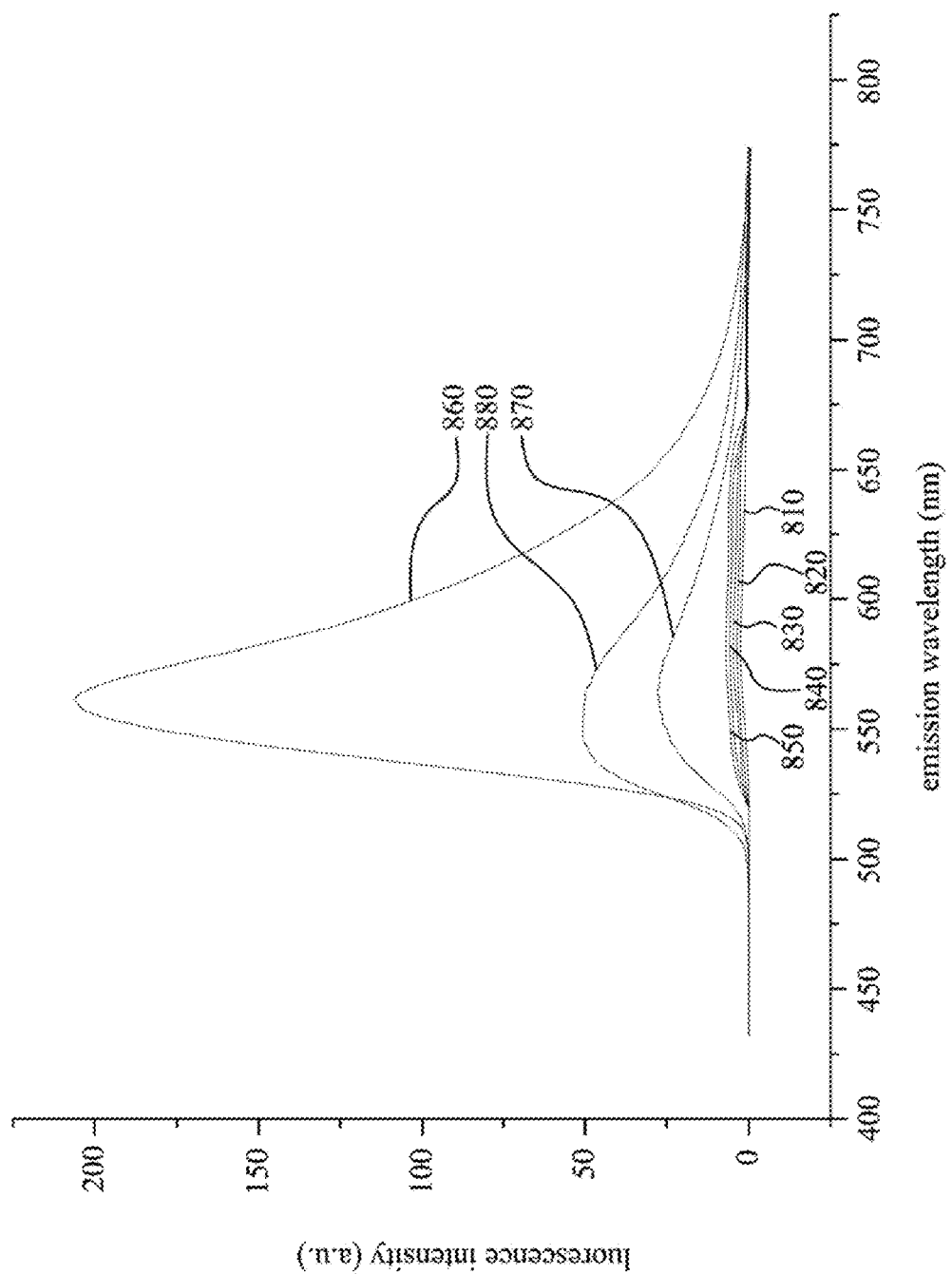
FIG. 8 illustrates a fluorescence intensity and an emission wavelength of the water-soluble peptide fluorescence material of formula (III-22) at different pH values.

Continuing in FIG. 8, which illustrates a fluorescence intensity and an emission wavelength of the water-soluble peptide fluorescence material of formula (III-22) at different pH values. In Experimental Examples 810, 820, 830, 840, 850, 860, 870 and 880, the water-soluble peptide fluorescence material of formula (III-22) is respectively placed in environments having a pH value of 10, 9, 8, 7, 6, 5, 4 and 3 for testing. In Experimental Examples 810 to 850, the water-soluble peptide fluorescence material is respectively placed in environments having the pH value of 10 to 6. As shown in FIG. 8, Experimental Examples 810 to 850 have low fluorescence intensities, so no significant fluorescence marker is shown. While the pH value is decreased to 5 (Experimental Example 860), the fluorescence intensity is significantly increased, and the emission peak is at about 575 nm to show the yellow fluorescence. Then, the fluorescence intensity of Experimental Example 870 is decreased when decreasing the pH value from 5 to 4, and the fluorescence intensity of Experimental Example 870 (pH=3) is slightly increased. Therefore, the water-soluble peptide fluorescence material of formula (III-22) has the highest fluorescence intensity at the pH value of 5. In addition, the fluorescence intensity of Experimental Example 860 (pH=5) is 90 times of the fluorescence intensity of Experimental Example 810 (pH=1), which represents that the water-soluble peptide fluorescence material has obvious light-emitting interval and easily to identify and detect positions of the acidic cells.

The product of Embodiment 23 has a structure of formula (III-23):

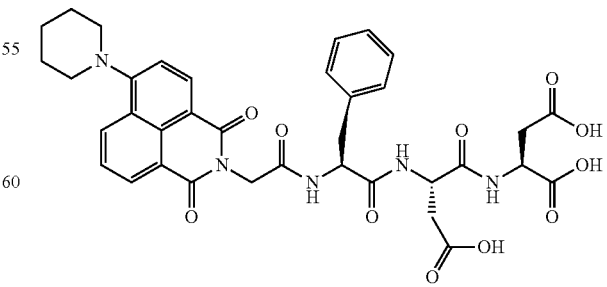

(III-23)

The NMR spectroscopy of the product in Embodiment 23 is shown below:

$^1$H NMR (300 MHz, DMSO-d6): δ=1.65-1.75 (br, 2H; CH$_2$), 1.80-1.90 (br, 4H; CH$_2$), 1.95-2.05 (q, J=9.7 Hz, 2H; CH$_2$), 2.25-2.35, (t, J=4.9 Hz, 2H; CH$_2$), 2.65-2.75 (m, 3H; CH$_2$), 2.95-3.15 (m, 1H, CH$_2$), 3.20-3.30 (br, 4H, CH$_2$), 4.15-4.25 (q, J=6.9 Hz, 1H; CH), 4.45-4.55 (q, J=12.1 Hz, 2H; CH), 4.60 (s, 3H; CH), 7.15-7.30 (m, 5H; CH), 7.30-7.40 (d, J=7.8 Hz, 1H; NH), 7.85 (t, J=8.1 Hz, 1H; CH), 7.95 (d, J=7.5 Hz, 1H; NH), 8.35 (d, J=8.1 Hz, 2H; CH), 8.45-8.55 (t, J=7.8 Hz, 3H; CH);

$^{13}$C NMR (75 MHz, DMSO-d6): δ=24.3, 26.1, 26.7, 36.1, 30.2, 36.4, 38.06, 42.4, 49.9, 51.7, 54.4, 115.2, 115.3, 122.8, 125.8, 126.2, 126.6, 128.4, 129.7, 132.4, 138.2, 157.3, 163.2, 163.8, 167.3, 170.9, 171.5, 172.0, 173.4, 174.2;

MS [ESI$^-$]: m/z (%): expected value: 729.73, experimental value: 728.30 [M-H]$^-$.

Figure 9:
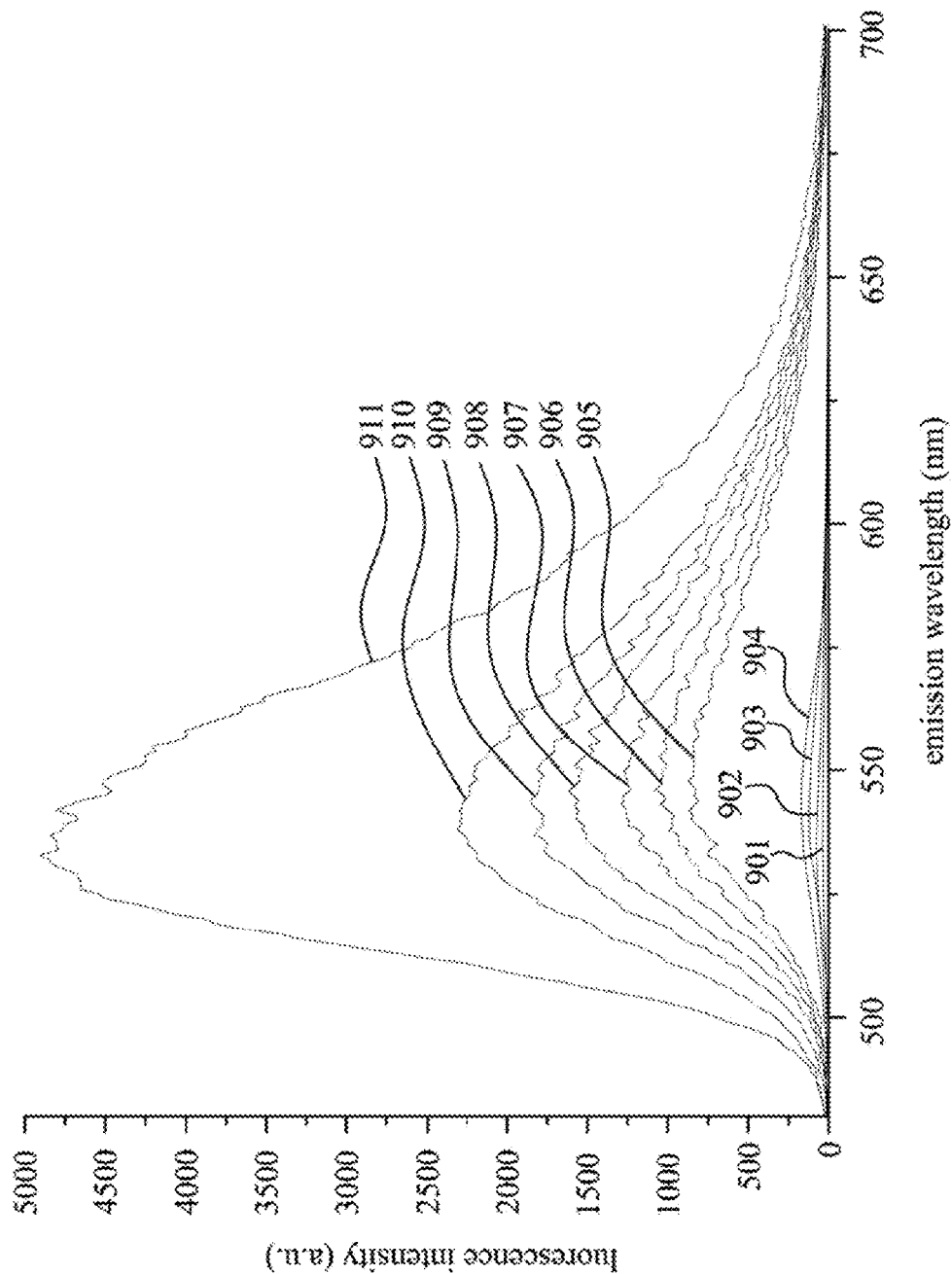
FIG. 9 illustrates a fluorescence intensity and an emission wavelength of the water-soluble peptide fluorescence material of formula (III-23) in co-solvents having different proportions of water and dimethyl sulfoxide.

Continuing in FIG. 9, which illustrates a fluorescence intensity and an emission wavelength of the water-soluble peptide fluorescence material of formula (III-23) in co-solvents having different proportions of water and dimethyl sulfoxide. In Experimental Examples 901, 902, 903, 904, 905, 906, 907, 908, 909 and 910, water respectively has 0, 10, 20, 30, 40, 50, 60, 70, 80 and 90% of a total volume of the co-solvent. As shown in FIG. 9, the water-soluble peptide fluorescence material of formula (III-23) has the highest fluorescence intensity in Experimental Example 910 to provide a more obvious fluorescence marker. Given the above, the fluorescence intensity of the water-soluble peptide fluorescence material of formula (III-23) is increased corresponding to the increase of the volume ratio of water and has a phenomenon of aggregation-induced emission in water. In addition, the water-soluble peptide fluorescence material of formula (III-23) has the emission wavelength of about 550 nm, so the observed fluorescence has a color of green.

Figure 10:
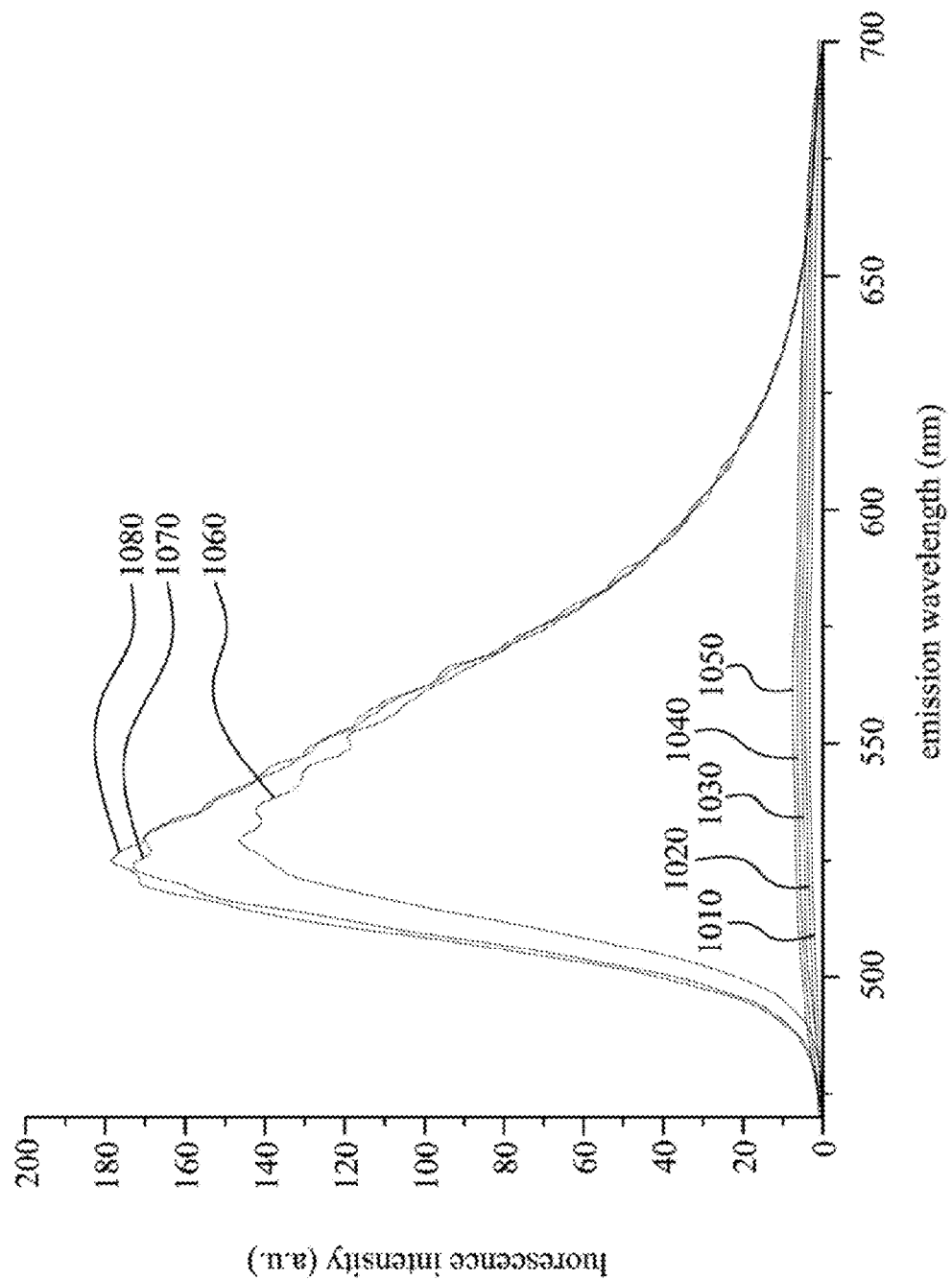
FIG. 10 illustrates a fluorescence intensity and an emission wavelength of the water-soluble peptide fluorescence material of formula (III-23) at different pH values.

FIG. 10 illustrates a fluorescence intensity and an emission wavelength of the water-soluble peptide fluorescence material of formula (III-23) at different pH values. In Experimental Examples 1010, 1020, 1030, 1040, 1050, 1060, 1070 and 1080, the water-soluble peptide fluorescence material of formula (III-23) is respectively placed in environments having a pH value of 10, 9, 8, 7, 6, 5, 4 and 3 for testing. In Experimental Examples 1010 to 1050, the water-soluble peptide fluorescence material is respectively placed in environments having the pH value of 10 to 6. As shown in FIG. 10, Experimental Examples 1010 to 1050 have low fluorescence intensities, so no significant fluorescence marker is shown. While the pH value is decreased to 5 (Experimental Example 1060), the fluorescence intensity is significantly increased, and the emission peak is at about 525 nm to show the green fluorescence. Then, the pH value is decreased to 4 and 3, and the fluorescence intensities of Experimental Examples 1070 and 1080 are slightly increased. The water-soluble peptide fluorescence material not only provides obvious marker, but also achieves the same effect of the fluorescence at a low concentration, and thereby reduces the costs.

2-4. Solid Phase Peptide Synthesis (Grafting Four Amino Acids)

Embodiments of grafting four amino acids is begun with swelling 2-chlorotrityl chloride resin (1.2 g, 1 mmol) in anhydrous dichloromethane (CH$_2$Cl$_2$) for 30 min, and a first amino acid having a Fmoc protective group is dissolved in anhydrous DMF and DIEA (0.83 ml, 5.0 mmol). Then, the first amino acid is reacted with the 2-chlorotrityl chloride resin for 1 hour to graft the first amino acid on the 2-chlorotrityl chloride resin. After that, piperidine (20% in DMF) is added and reacted for 20 minutes to remove the Fmoc protective group on the first amino acid, and the above step is repeated twice (2 minutes each time).

Subsequently, a second amino acid having a Fmoc protective group, DIEA (0.83 ml, 5.0 mmol) and HBTU (0.76 g, 2.0 mmol) are dissolved in anhydrous DMF and reacted with the 2-chlorotrityl chloride resin for 30 minutes. During the reaction, the HBTU acts as a coupling agent to make the second amino acid couple to a free amino group (the Fmoc protective group thereon is removed) of the first amino acid. Then, piperidine (20% in DMF) is again added and reacted for 20 minutes, and the above step is repeated twice (2 minutes each time) to remove the Fmoc protective group on the second amino acid.

Subsequently, a third amino acid having a Fmoc protective group, DIEA (0.83 ml, 5.0 mmol) and HBTU (0.76 g, 2.0 mmol) are dissolved in anhydrous DMF and reacted with the 2-chlorotrityl chloride resin for 30 minutes. During the reaction, the HBTU acts as the coupling agent to make the third amino acid couple to a free amino group (the Fmoc protective group thereon is removed) of the second amino acid. In order to remove the Fmoc protective group on the third amino acid, piperidine (20% in DMF) is added and reacted for 20 minutes, and the above step is repeated twice (2 minutes each time).

Then, a fourth amino acid having a Fmoc protective group, DIEA (0.83 ml, 5.0 mmol) and HBTU (0.76 g, 2.0 mmol) are dissolved in anhydrous DMF and reacted with the 2-chlorotrityl chloride resin for 30 minutes. During the reaction, the HBTU acts as the coupling agent to make the fourth amino acid couple to a free amino group (the Fmoc protective group thereon is removed) of the third amino acid. As the same step mentioned above, the Fmoc protective group on the fourth amino acid is removed by adding piperidine (20% in DMF) to react for 20 minutes, and the above step is repeated twice (2 minutes each time).

After that, the terminal luminophore, DIEA (0.83 ml, 5.0 mmol) and HBTU (0.76 g, 2.0 mmol) are dissolved in anhydrous DMF and reacted with the 2-chlorotrityl chloride resin. During the reaction, the HBTU acts as the coupling agent to make the terminal luminophore couple to a free amino group (the Fmoc protective group thereon is removed) of the fourth amino acid.

The reaction mixture is stirred overnight, and then the water-soluble peptide fluorescence material is cleaved from the 2-chlorotrityl chloride resin through treatment of trifluoroacetic acid (90% in deionized water) for 3 hours. The resulting solution is further dried under a stream of air, and diethyl ether is added to precipitate a target product. Then, the precipitate is dried under vacuum to remove residual solvent, and the remained solid product is the water-soluble peptide fluorescence material, which is under structure analysis by a nuclear magnetic resonance ($^1$H NMR and $^{13}$C NMR). Continuing in Table 5, which shows different water-soluble peptide fluorescence materials synthesized from four amino acids and various terminal luminophores.

TABLE 5

Different water-soluble peptide fluorescence materials
synthesized from four amino acids and various terminal luminophores.

| Embodiment | first amino acid (weight, mol) | second amino acid (weight, mol) | third amino acid (weight, mol) | fourth amino acid (weight, mol) | terminal luminophore (weight, mol) | structure of the product (color, weight) |
|---|---|---|---|---|---|---|
| Embodiment 24 | Fmoc-O-tert-butyl-L-tyrosine (0.92 g, 2.0 mmol) | Fmoc-L-glycine (0.6 g, 2.0 mmol) | Fmoc-L-glycine (0.6 g, 2.0 mmol) | Fmoc-L-glycine (0.6 g, 2.0 mmol) | NI (0.77 g, 3.0 mmol) | III-24 (white solid, 0.42 g) |
| Embodiment 25 | Fmoc-O-tert-butyl-L-aspartic acid (0.92 g, 2.0 mmol) | Fmoc-L-glycine (0.6 g, 2.0 mmol) | Fmoc-Pbf-L-arginine (1.3 g, 2.0 mmol) | Fmoc-L-phenylalanine (0.78 g, 2.0 mmol) | NI (0.51 g, 2.0 mmol) | III-25 (white solid, 0.29 g) |
| Embodiment 26 | Fmoc-L-aspartic acid (0.62 g, 1.5 mmol) | Fmoc-L-aspartic acid (0.62 g, 1.5 mmol) | Fmoc-L-aspartic acid (0.62 g, 1.5 mmol) | Fmoc-L-phenylalanine (0.58 g, 1.5 mmol) | PPNI (0.677 g, 2.0 mmol) | III-26 (brown solid, 0.734 g) |
| Embodiment 27 | Fmoc-L-glutamic acid (0.425 g, 1.0 mmol) | Fmoc-L-glutamic acid (0.425 g, 1.0 mmol) | Fmoc-L-glutamic acid (0.425 g, 1.0 mmol) | Fmoc-L-phenylalanine (0.387 g, 1.0 mmol) | PPNI (0.4365 g, 1.0 mmol) | III-27 (yellow solid, 0.350 g) |

The product of Embodiment 24 has a structure of formula including a peptide sequence Gly-Gly-Gly-Tyr (SEQ ID NO: 1) (III-24):

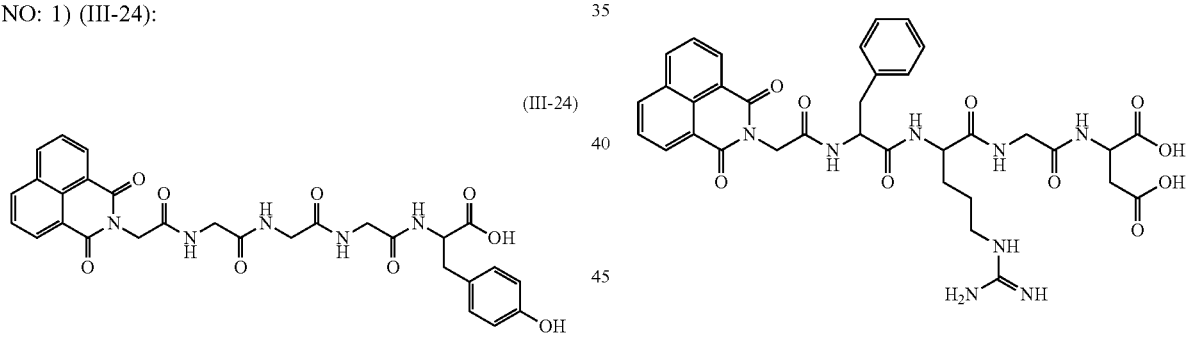

The NMR spectroscopy of the product in Embodiment 24 is shown below:

$^1$H NMR (300 MHz, DMSO-d6): δ=2.75-2.85 (m, 1H; $CH_2$), 2.90-3.00 (m, 1H; $CH_2$), 3.65-3.90 (m, 6H; $CH_2$), 4.30-4.45 (m, 1H; CH), 4.781 (s, 2H; $CH_2$), 6.69 (d, J=8.9 Hz, 2H; CH), 7.04 (d, J=8.1 Hz, 2H; CH), 7.91 (t, J=7.65 Hz, 2H; CH), 8.05-8.20 (m, 2H; NH), 8.20-8.30 (m, 1H; NH), 8.45-8.60 (m, 5H; CH, NH);

$^{13}$C NMR (75 MHz, DMSO-d6): δ=37.1, 42.6, 42.9, 43.0, 43.3, 54.9, 116.0, 122.9, 128.2, 128.4, 131.0, 131.8, 132.3, 135.5, 156.9, 164.3, 168.2, 169.3, 169.9, 170.0, 173.9;

MS [ESI$^-$]: m/z (%): expected value: 589.18, experimental value: 588.2 [M-H]$^-$.

The product of Embodiment 25 has a structure of formula including a peptide sequence Phe-Arg-Gly-Asp (SEQ ID NO: 2) (III-25):

The NMR spectroscopy of the product in Embodiment 25 is shown below:

$^1$H NMR (300 MHz, DMSO-d6): δ=1.45-1.70 (m, 3H; $CH_2$), 1.70-1.85 (m, 1H; $CH_2$), 2.60-2.70 (m, 2H; $CH_2$), 2.80-2.95 (m, 1H; $CH_2$), 3.00-3.20 (m, 3H; $CH_2$), 3.65-3.90 (m, 2H; $CH_2$), 4.25-4.40 (m, 1H; CH), 4.45-4.65 (m, 1H; CH), 4.706 (s, 2H; $CH_2$), 7.20-7.35 (m, 5H; CH), 7.91 (t, J=7.65 Hz, 2H; CH), 8.10-8.20 (m, 1H; NH), 8.20-8.30 (m, 1H; NH), 8.45-8.60 (m, 5H; CH, NH);

$^{13}$C NMR (75 MHz, DMSO-d6): δ=25.8, 30.2, 37.5, 38.3, 42.7, 43.2, 49.6, 53.3, 55.0, 122.8, 127.2, 128.2, 128.4, 129.0, 130.3, 131.8, 132.3, 135.5, 138.6, 157.7, 164.2, 167.6, 169.4, 172.0, 172.4, 172.9, 173.4;

MS [ESI$^-$]: m/z (%): expected value: 730.27, experimental value: 731.3 [M-H]$^-$.

The product of Embodiment 26 has a structure of formula including a peptide sequence Phe-Asp-Asp-Asp (SEQ ID NO: 3) (III-26):

(III-26)

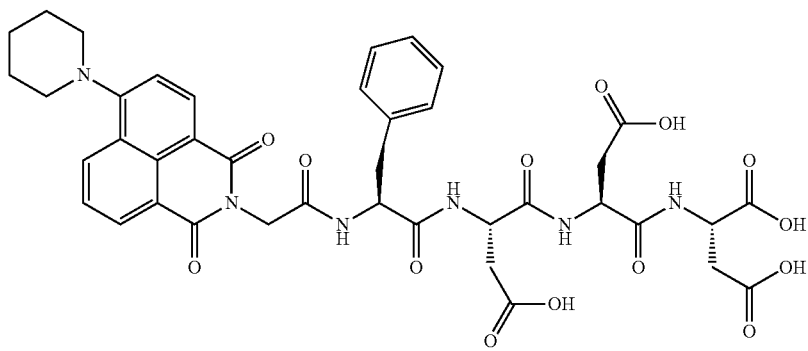

The NMR spectroscopy of the product in Embodiment 26 is shown below:

$^1$H NMR (300 MHz, DMSO-d6): δ=1.65-1.75 (br, 2H; CH$_2$), 1.80-1.90 (br, 4H; CH$_2$), 2.55-2.90 (m, 7H; CH$_2$), 3.00-3.10 (m, 1H; CH$_2$), 3.20-3.30 (br, 4H; CH$_2$), 4.55-4.65 (m, 4H; CH), 4.67 (s, 2H; CH$_2$), 7.20-7.25 (m, 1H; CH), 7.25-7.35 (m, 4H; CH), 7.36 (d, J=8.4 Hz, 1H; NH), 7.85 (t, J=7.95 Hz, 1H; NH), 7.99 (d, J=8.1 Hz, 1H; NH), 8.14 (d, J=8.1 Hz, 1H; NH), 8.35-8.55 (m, 5H; CH);

$^{13}$C NMR (75 MHz, DMSO-d6): δ=23.9, 25.8, 36.0, 36.1, 36.2, 37.7, 42.2, 48.7, 49.4, 49.7, 53.9, 54.1, 114.8, 115.0, 122.4, 125.5, 125.9, 126.3, 128.1, 129.40, 129.44, 130.8, 132.5, 137.8, 157.0, 158.2, 158.7, 162.9, 163.5, 166.9, 170.3, 170.5, 171.2, 171.8, 171.9, 172.2;

MS [ESI$^-$]: m/z (%): expected value: 830.28, experimental value: 829.2 [M-H]$^-$.

The product of Embodiment 27 has a structure of formula including a peptide sequence Phe-Glu-Glu-Glu (SEQ ID NO: 4) (III-27):

$^{13}$C NMR (75 MHz, DMSO-d6): δ=24.5, 26.4, 26.8, 28.0, 28.2, 30.6, 30.7, 30.8, 38.0, 42.7, 51.9, 52.3, 52.6, 54.5, 54.6, 115.5, 115.6, 123.1, 126.1, 126.5, 126.9, 128.7, 129.9, 131.4, 133.1, 138.4, 157.6, 163.5, 164.1, 167.5, 171.5, 171.6, 171.8;

MS [ESI$^-$]: m/z (%): expected value: 872.87, experimental value: 871.2 [M-H]$^-$.

Figure 11:
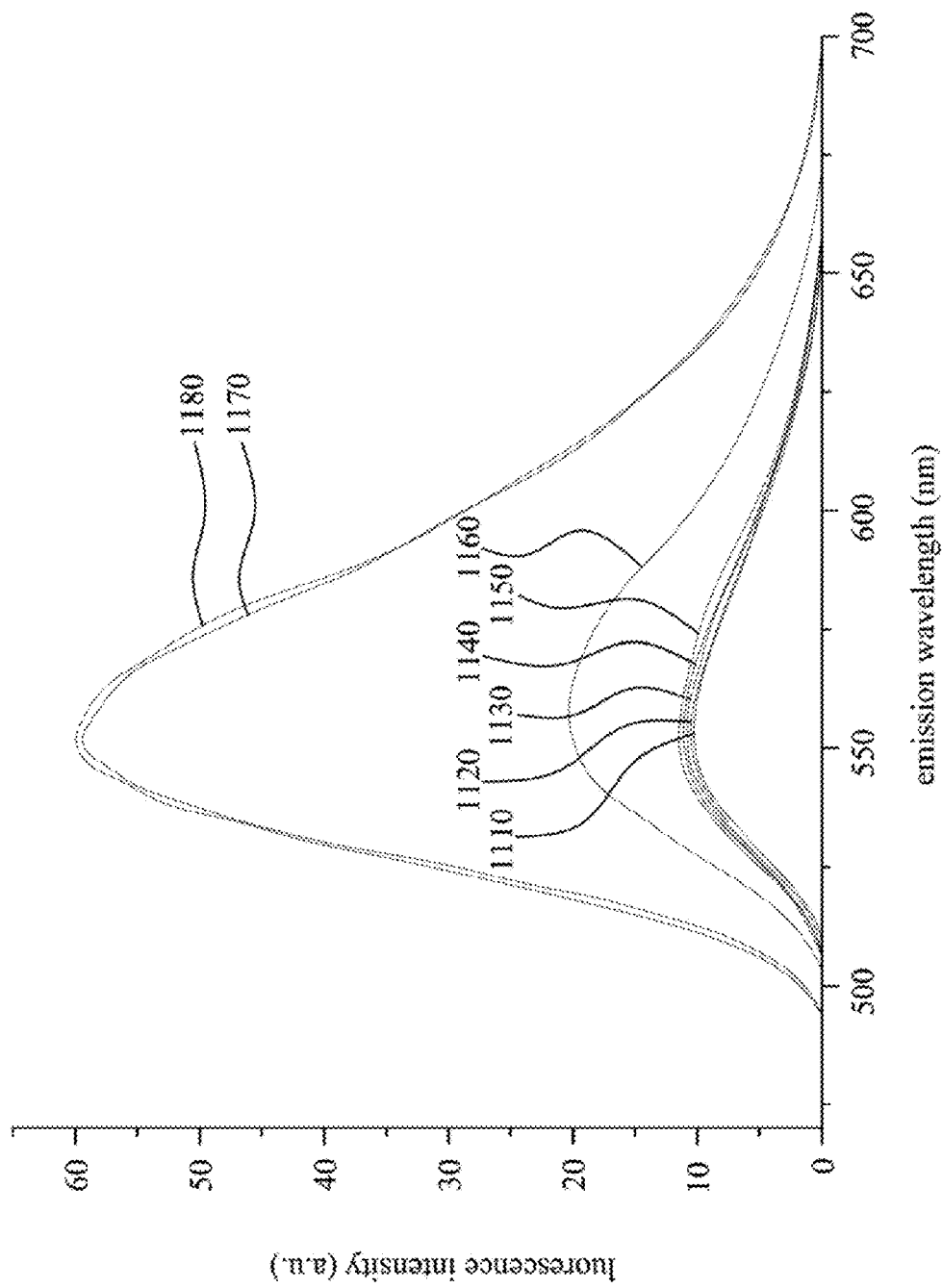
FIG. 11 illustrates a fluorescence intensity and an emission wavelength of the water-soluble peptide fluorescence material of formula (III-27) at different pH values.

FIG. 11 illustrates a fluorescence intensity and an emission wavelength of the water-soluble peptide fluorescence material of formula (III-27) at different pH values. In Experimental Examples 1110, 1120, 1130, 1140, 1150, 1160, 1170 and 1180, the water-soluble peptide fluorescence material of formula (III-27) is respectively placed in environments having a pH value of 10, 9, 8, 7, 6, 5, 4 and 3 for testing. In Experimental Examples 1110 to 1150, the water-soluble peptide fluorescence material is respectively placed in environments having the pH value of 10 to 6. As shown in FIG. 11, Experimental Examples 1110 to 1150 have low (III-27)

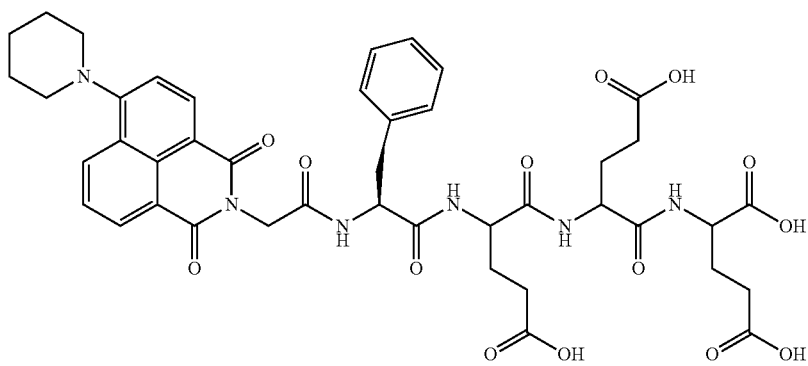

The NMR spectroscopy of the product in Embodiment 27 is shown below:

$^1$H NMR (300 MHz, DMSO-d6): δ=1.65-1.75 (br, 2H; CH$_2$), 1.80-1.90 (br, 4H; CH$_2$), 1.90-2.05 (q, J=9.0 Hz, 5H; CH$_2$), 2.25-2.35 (t, J=8.1 Hz, 7H; CH$_2$), 2.75-2.85 (m, 1H; CH$_2$), 3.00-3.10 (m, 1H; CH$_2$), 3.20-3.30 (br, 4H; CH$_2$), 4.20-4.30 (q, J=7.7 Hz, 1H; CH), 4.30-4.40 (q, J=10.8 Hz, 2H; CH), 4.55-4.65 (m, 1H; CH), 4.65 (s, 2H; CH$_2$), 7.20-7.25 (m, 1H; CH), 7.25-7.30 (m, 4H; CH), 7.35 (d, J=8.1 Hz, 1H; NH), 7.85 (t, J=7.95 Hz, 1H; CH), 8.00 (d, J=7.2 Hz, 1H; NH), 8.20 (d, J=7.8 Hz, 2H; NH), 8.4-8.55 (m, 4H; CH);

fluorescence intensities, so no significant fluorescence marker is shown. While the pH value is decreased to 5 (Experimental Example 1160), the fluorescence intensity is significantly increased, and the emission peak is at about 525 nm to show the green fluorescence. Then, the pH value is decreased to 4 and 3, and the fluorescence intensities of Experimental Examples 1170 and 1180 are significantly increased. The water-soluble peptide fluorescence material not only provides obvious marker, but also achieves the same effect of the fluorescence at a low concentration, and thereby reduces the costs.

2-5. Solid Phase Peptide Synthesis (Grafting Five Amino Acids)

Refer to embodiments of grafting four amino acids mentioned in 2-4 to understand embodiments of grafting five amino acids. Before grafting the terminal luminophore, a step of grafting a fifth amino acid is performed in a way the same as grafting the fourth amino acid, and the details are not described herein. The product is also under structure analysis by a nuclear magnetic resonance ($^1$H NMR and $^{13}$C NMR). Continuing in Table 6, which shows different water-soluble peptide fluorescence materials synthesized from five amino acids and various terminal luminophores.

Figure 12:
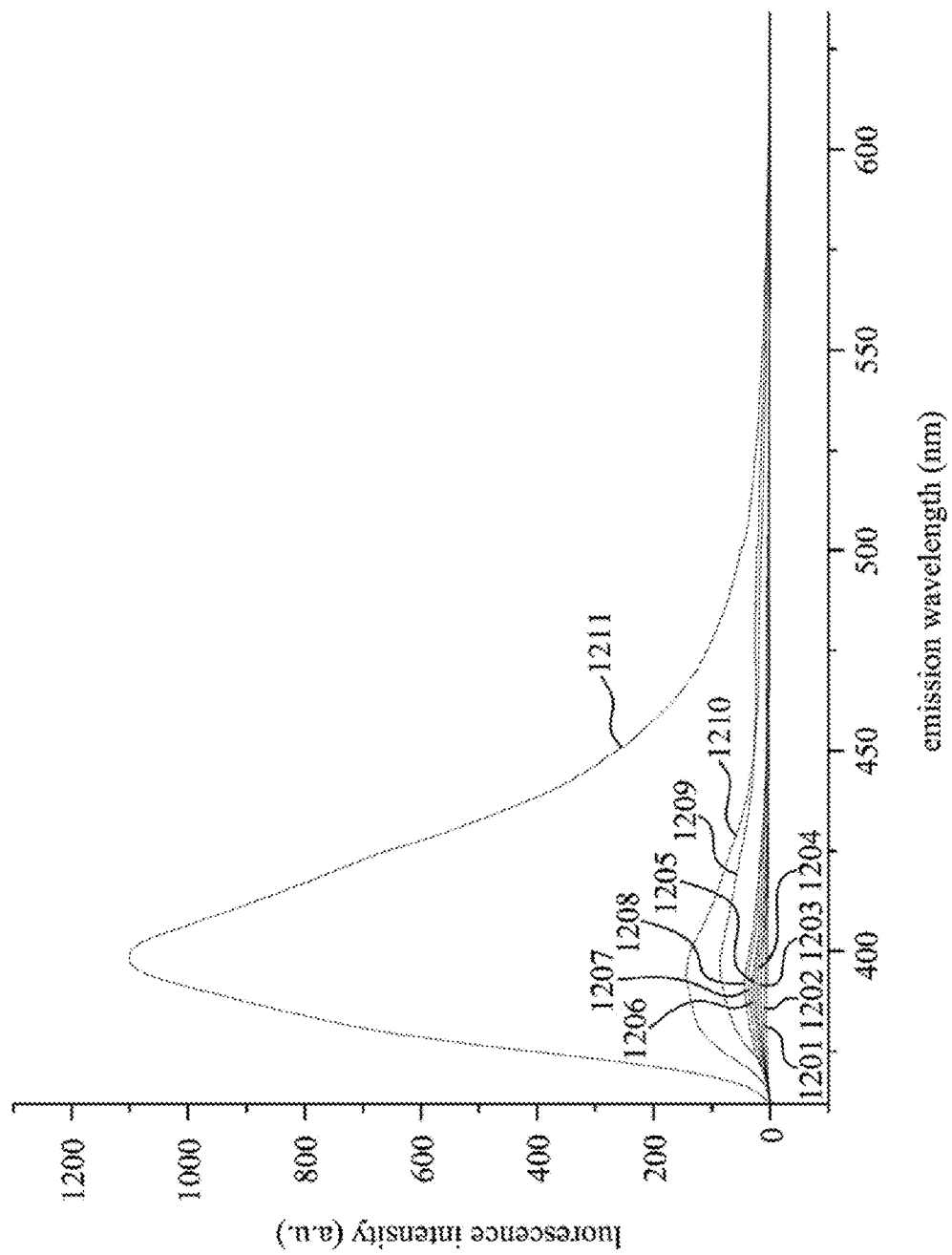
FIG. 12 illustrates a fluorescence intensity and an emission wavelength of the water-soluble peptide fluorescence material of formula (III-28) in co-solvents having different proportions of water and dimethyl sulfoxide.

FIG. 12 illustrates a fluorescence intensity and an emission wavelength of the water-soluble peptide fluorescence material of formula (III-28) in co-solvents having different proportions of water and dimethyl sulfoxide. In Experimental Example 1201, 1202, 1203, 1204, 1205, 1206, 1207, 1208, 1209, 1210 and 1211, water respectively has 0, 10, 20, 30, 40, 50, 60, 70, 80, 90 and 99% of a total volume of the co-solvent. As shown in FIG. 12, the water-soluble peptide fluorescence material of formula (III-28) has low fluorescence intensity in co-solvents of Experimental Examples 1201 to 1209. As such, no significant fluorescence marker is shown, so it is difficult to observe apparent fluorescence

TABLE 6

Different water-soluble peptide fluorescence materials synthesized from five amino acids and various terminal luminophores.

| Embodiment | first amino acid (weight, mol) | second amino acid (weight, mol) | third amino acid (weight, mol) | fourth amino acid (weight, mol) | fifth amino acid (weight, mol) | terminal luminophore (weight, mol) | structure of the product (color, weight) |
|---|---|---|---|---|---|---|---|
| Embodiment 28 | Fmoc-L-alanine (0.623 g, 2.0 mmol) | Fmoc-L-glutamic acid (0.851 g, 2.0 mmol) | Fmoc-L-glycine (0.6 g, 2.0 mmol) | Fmoc-L-aspartic acid (0.823 g, 2.0 mmol) | Fmoc-L-phenylalanine (0.78 g, 2.0 mmol) | NI (0.77 g, 3.0 mmol) | III-28 (white solid, 0.05 g) |
| Embodiment 29 | Fmoc-L-alanine (0.623 g, 2.0 mmol) | Fmoc-L-glutamic acid (0.851 g, 2.0 mmol) | Fmoc-L-glycine (0.6 g, 2.0 mmol) | Fmoc-L-aspartic acid (0.823 g, 2.0 mmol) | Fmoc-L-phenylalanine (0.78 g, 2.0 mmol) | PPNI (1.02 g, 3.0 mmol) | III-29 (yellow solid, 0.6956 g) |

The product of Embodiment 28 has a structure of formula including a peptide sequence Phe-Asp-Gly-Glu-Ala (SEQ ID NO: 5) (III-28):

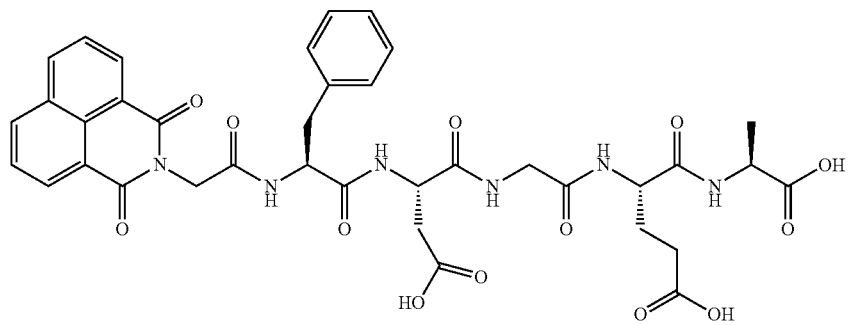

(III-28)

Figure 13:
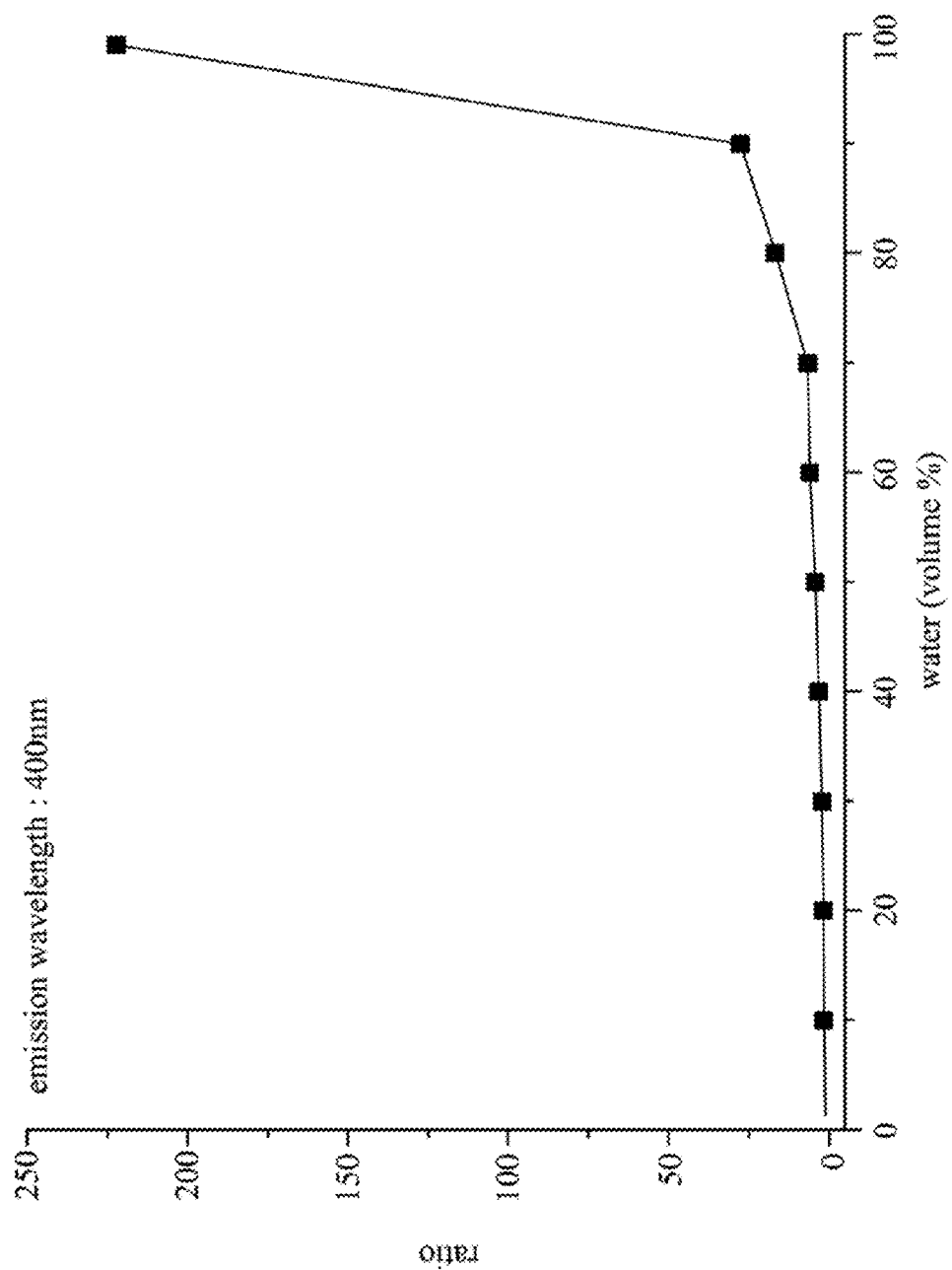
FIG. 13 depicts a ratio of the fluorescence intensity between Experimental Examples 1202 to 1211 and Experimental Example 1201, at the emission wavelength of 400 nm.

The NMR spectroscopy of the product in Embodiment 28 is shown below:

$^1$H NMR (300 MHz, DMSO-d6): δ=1.29 (d, J(H, H)=7.2 Hz, 3H; CH3), 1.70-1.90 (m, 1H; CH$_2$), 1.85-2.05 (m, 1H; CH$_2$), 2.29 (t, J(H, H)=8.25 Hz, 2H; CH$_2$), 2.70-2.90 (m, 2H; CH$_2$), 3.00-3.15 (m, 1H; CH$_2$), 3.65-3.85 (m, 2H; CH$_2$), 4.15-4.30 (m, 1H; CH), 4.30-4.40 (m, 1H; CH), 4.50-4.65 (m, 2H; CH), 4.78 (s, 2H; CH$_2$), 7.20-7.30 (m, 5H; CH), 7.93 (t, J(H, H)=7.8 Hz, 4H; CH), 8.29 (d, J(H, H)=7.2 Hz, 1H; NH), 8.40-8.65 (m, 6H; NH, CH);

$^{13}$C NMR (75 MHz, DMSO-d6): δ=17.8, 28.5, 30.9, 36.9, 38.4, 43.1, 48.4, 50.6, 52.4, 54.9, 122.8, 127.2, 128.2, 128.4, 129.0, 130.2, 131.8, 132.3, 135.5, 138.5, 164.2, 167.6, 169.2, 171.6, 171.7, 172.0, 172.7, 174.8, 175.0;

MS [ESI$^-$]: m/z (%): expected value: 774.25, experimental value: 773.3 [M-H]$^-$.

visually. While a volume ratio of water is increased to 90% (Experimental Example 1210), the fluorescence intensity is significantly increased to 150 fluorescent units. The volume ratio of water is further increased to 99%, and the fluorescence intensity of Experimental Example 1211 is sharply increased to about 110 fluorescent units, so as to provide a more obvious fluorescence marker. Given the above, the fluorescence intensity of the water-soluble peptide fluorescence material of formula (III-28) is increased corresponding to the increase of the volume ratio of water and has a phenomenon of aggregation-induced emission in water. In addition, the water-soluble peptide fluorescence material of formula (III-28) has the emission wavelength of about 400 nm, so the observed fluorescence has a color of violet. FIG. 13 depicts a ratio of the fluorescence intensity between Experimental Examples 1202 to 1211 and Experimental Example 1201, at the emission wavelength of 400 nm. As shown in FIG. 13, the fluorescence intensity of Experimental Example 1211 is 225 times of the fluorescence intensity of Experimental Example 1201.

Figure 14:
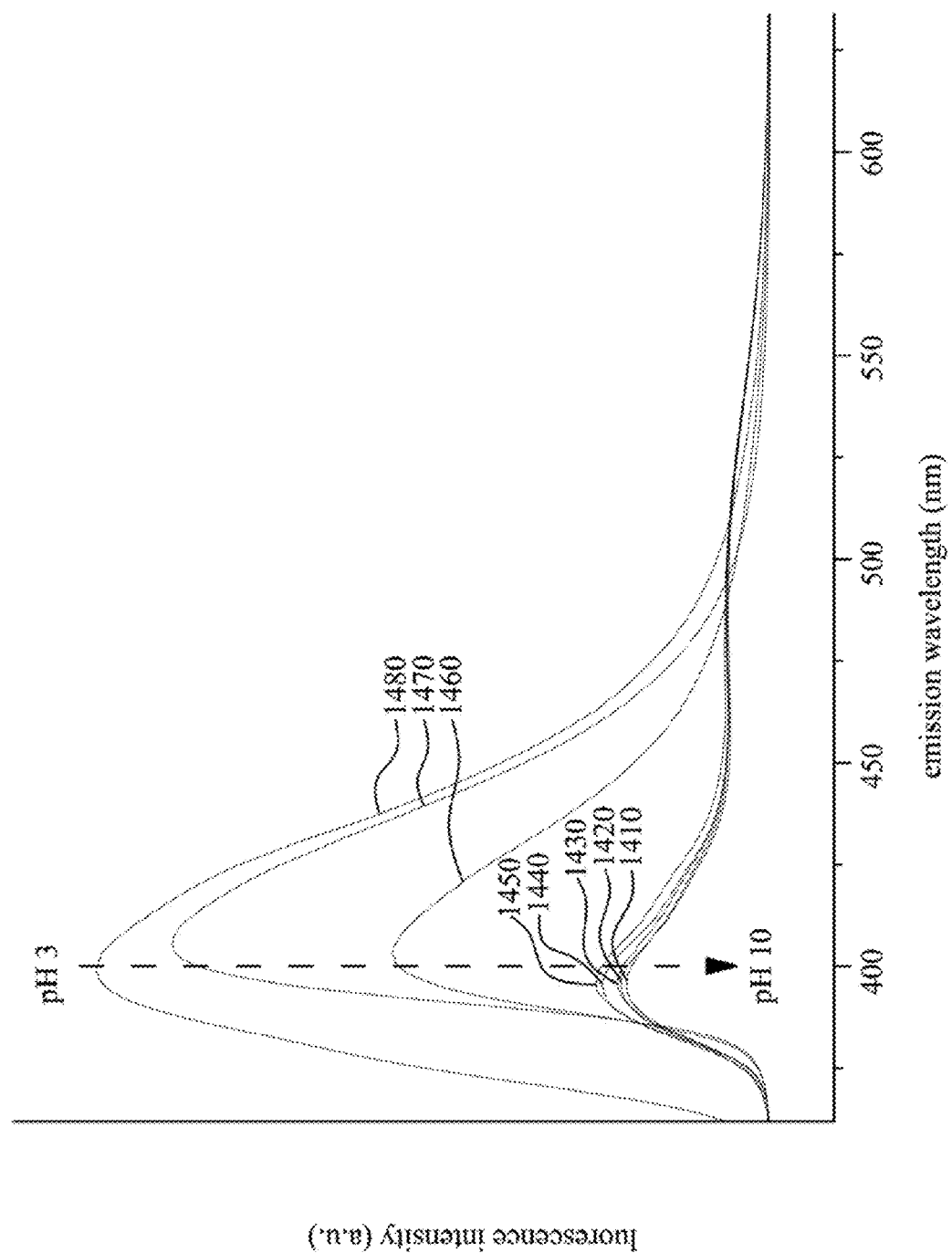
FIG. 14 illustrates a fluorescence intensity and an emission wavelength of the water-soluble peptide fluorescence material of formula (III-28) at different pH values.

FIG. 14 illustrates a fluorescence intensity and an emission wavelength of the water-soluble peptide fluorescence material of formula (III-28) at different pH values. In Experimental Examples 1410, 1420, 1430, 1440, 1450, 1460, 1470 and 1480, the water-soluble peptide fluorescence material of formula (III-28) is respectively placed in environments having a pH value of 10, 9, 8, 7, 6, 5, 4 and 3 for testing. In Experimental Examples 1410 to 1450, the water-soluble peptide fluorescence material is respectively placed in environments having the pH value of 10 to 6. As shown in FIG. 14, Experimental Examples 1410 to 1450 have low fluorescence intensities, so no significant fluorescence marker is shown. While the pH value is decreased to 5 (Experimental Example 1460), the fluorescence intensity is significantly increased, and the emission peak is at about 400 nm to show the purple fluorescence. Then, the pH value is decreased to 4 and 3, and the fluorescence intensities of Experimental Examples 1470 and 1480 are significantly increased. The water-soluble peptide fluorescence material not only provides obvious marker, but also achieves the same effect of the fluorescence at a low concentration, and thereby reduces the costs.

The product of Embodiment 29 has a structure of formula including a peptide sequence Phe-Asp-Gly-Glu-Ala (SEQ ID NO: 6) (III-29):

2.27 (br, 4H; $CH_2$), 1.90-2.05 (m, 1H; $CH_2$), 2.30 (t, J(H, H)=8.1 Hz, 2H; $CH_2$), 2.55-2.65 (m, 1H; $CH_2$), 2.70-2.95 (m, 2H; $CH_2$), 3.00-3.15 (m, 1H; $CH_2$), 3.25 (br, 4H; $CH_2$), 3.65-3.85 (m, 2H; $CH_2$), 4.10-4.25 (m, 1H; CH), 4.30-4.40 (m, 1H; CH), 4.50-4.65 (m, 2H; CH), 4.69 (s, 2H; $CH_2$), 7.20-7.30 (m, 5H; CH), 7.35 (d, J(H, H)=8.4 Hz, 1H; NH), 7.80-8.00 (m, 3H; CH), 8.29 (d, J(H, H)=7.2 Hz, 1H; NH), 8.35-8.60 (m, 5H; NH, CH);

$^{13}$C NMR (75 MHz, DMSO-d6): δ=17.8, 24.8, 26.6, 28.5, 30.9, 36.8, 38.4, 43.0, 43.2, 48.4, 50.6, 52.3, 54.9, 115.7, 115.9, 123.3, 126.4, 126.8, 127.2, 129.0, 130.2, 131.4, 131.7, 133.4, 138.5, 157.8, 163.8, 164.4, 167.8, 169.2, 171.6, 171.7, 172.0, 172.7, 174.8, 175.0;

MS [ESI$^-$]: m/z (%): expected value: 857.32, experimental value: 856.60 [M-H]$^-$.

2-6. Solid Phase Peptide Synthesis (Grafting Six Amino Acids)

Refer to embodiments of grafting four amino acids mentioned in 2-4 to understand embodiments of grafting six amino acids. Before grafting the terminal luminophore, a step of grafting a fifth amino acid and a sixth amino acid is performed in a way the same as grafting the fourth amino acid, and the details are not described herein. The product is also under structure analysis by a nuclear magnetic reso-

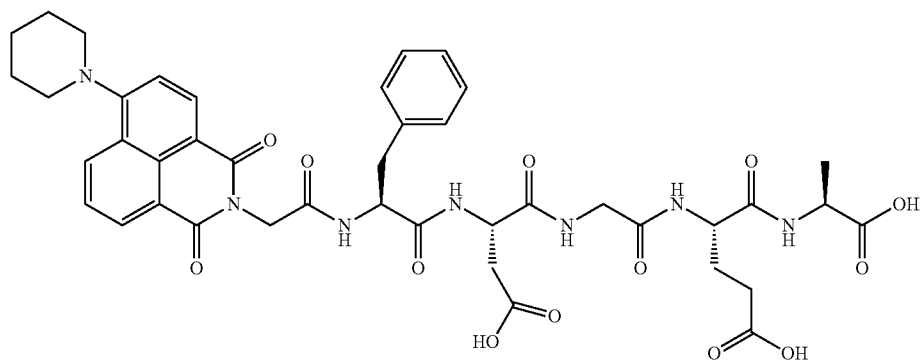

(III-29)

The NMR spectroscopy of the product in Embodiment 29 is shown below:

$^1$H NMR (300 MHz, DMSO-d6): δ=1.30 (d, J(H, H)=7.2 Hz, 3H; $CH_3$), 1.71 (br, 2H; $CH_2$), 1.75-1.85 (m, 1H; $CH_2$), nance ($^1$H NMR and $^{13}$C NMR). Continuing in Table 7, which shows different water-soluble peptide fluorescence materials synthesized from five amino acids and various terminal luminophores.

TABLE 7

Different water-soluble peptide fluorescence materials synthesized from six amino acids and various terminal luminophores

| Embodiment | first amino acid (weight, mol) | second amino acid (weight, mol) | third amino acid (weight, mol) | fourth amino acid (weight, mol) | fifth amino acid (weight, mol) | sixth amino acid (weight, mol) | terminal luminophore (weight, mol) | structure of the product (color, weight) |
|---|---|---|---|---|---|---|---|---|
| Embodiment 30 | Fmoc-O-tert-butyl-L-tyrosine (0.92 g, 2.0 mmol) | Fmoc-L-glycine (0.6 g, 2.0 mmol) | Fmoc-L-glycine (0.6 g, 2.0 mmol) | Fmoc-L-glycine (0.6 g, 2.0 mmol) | Fmoc-L-glycine (0.6 g, 2.0 mmol) | Fmoc-L-glycine (0.6 g, 2.0 mmol) | NI (0.51 g, 2.0 mmol) | III-30 (white solid, 0.20 g) |
| Embodiment 31 | Fmoc-L-valine (0.68 g, 2.0 mmol) | Fmoc-L-alanine (0.622 g, 2.0 mmol) | Fmoc-L-valine (0.68 g, 2.0 mmol) | Fmoc-L-lysine (0.94 g, 2.0 mmol) | Fmoc-L-isolucine (0.71 g, 2.0 mmol) | Fmoc-L-phenylalanine (0.78 g, 2.0 mmol) | NI (0.79 g, 3.0 mmol) | III-31 (white solid, 0.92 g) |

The product of Embodiment 30 has a structure of formula including a peptide sequence Gly-Gly-Gly-Gly-Gly-Tyr (SEQ ID NO: 7) (III-30):

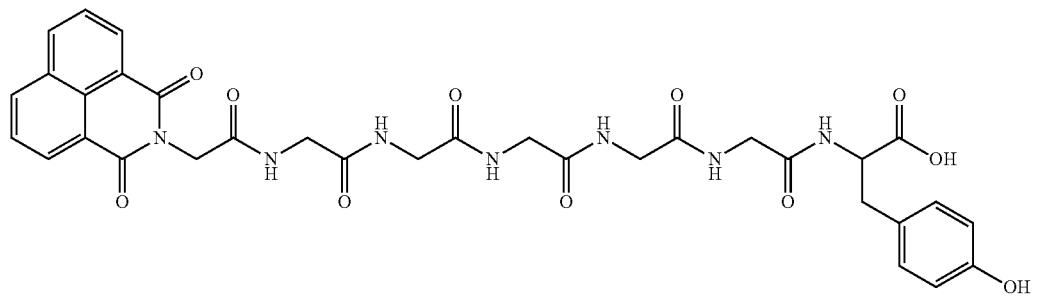

(III-30)

The NMR spectroscopy of the product in Embodiment 30 is shown below:

¹H NMR (300 MHz, DMSO-d6): δ=2.70-3.05 (m, 2H; $CH_2$), 3.60-3.90 (m, 10H; $CH_2$), 4.30-4.40 (m, 1H; CH), 4.70-4.80 (m, 2H; $CH_2$), 6.68 (d, J=8.4 Hz, 2H; CH), 7.03 (d, J=8.4 Hz, 2H; CH), 7.94 (t, J=7.8 Hz, 2H; CH), 8.00-8.10 (m, 2H; NH), 8.10-8.25 (m, 3H; NH), 8.50-8.65 (m, 4H; CH);

¹³C NMR (75 MHz, DMSO-d6): δ=37.0, 42.2, 42.5, 43.0, 43.3, 54.8, 116.0, 122.9, 128.2, 128.3, 128.4, 128.5, 131.0, 131.8, 135.5, 156.9, 164.3, 168.2, 169.5, 169.9, 170.07, 170.13, 170.3, 173.9;

MS [ESI⁻]: m/z (%): expected value: 703.22, experimental value: 702.0[M-H]⁻.

Figure 15:
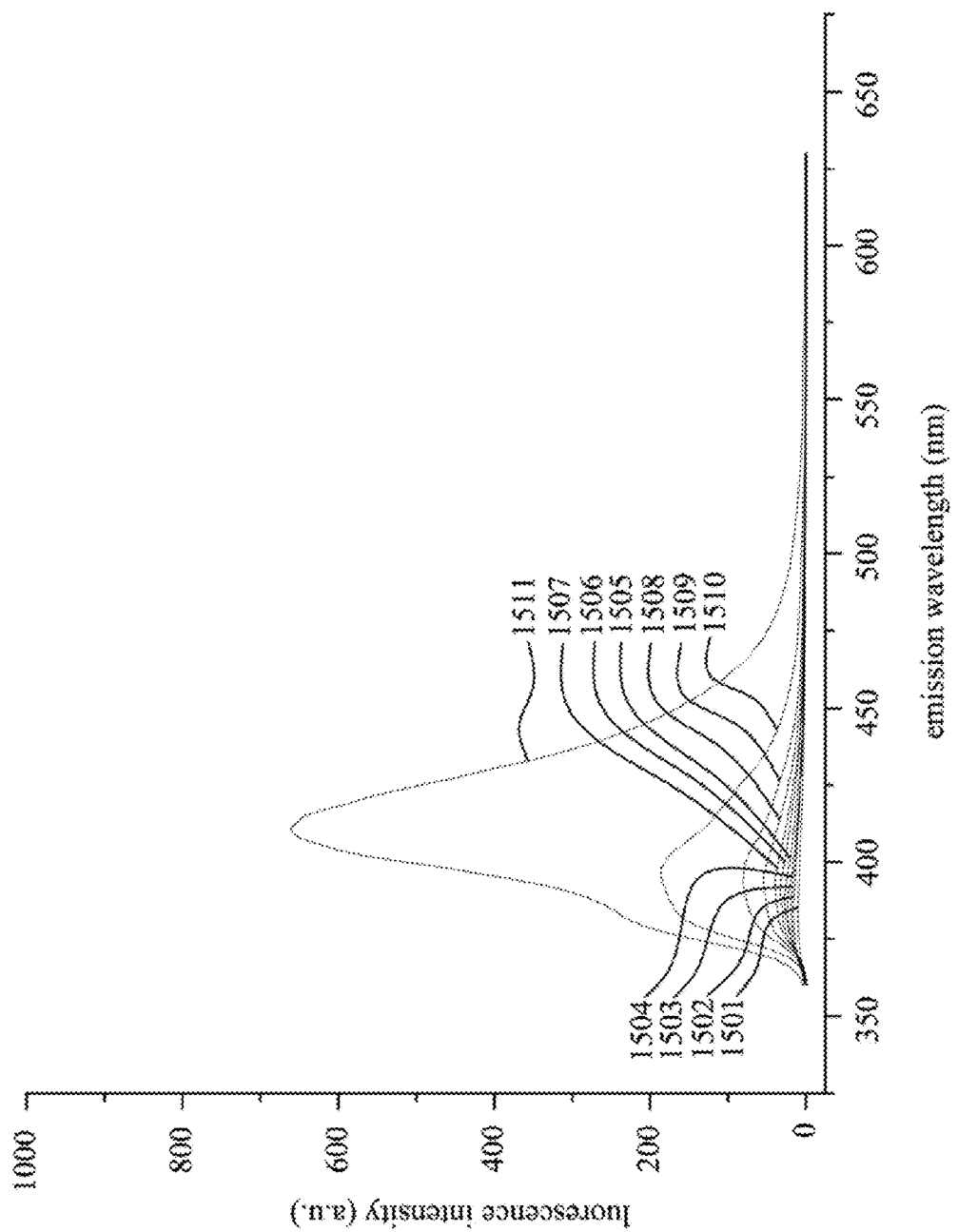
FIG. 15 illustrates a fluorescence intensity and an emission wavelength of the water-soluble peptide fluorescence material of formula (III-30) in co-solvents having different proportions of water and dimethyl sulfoxide.
Figure 16:
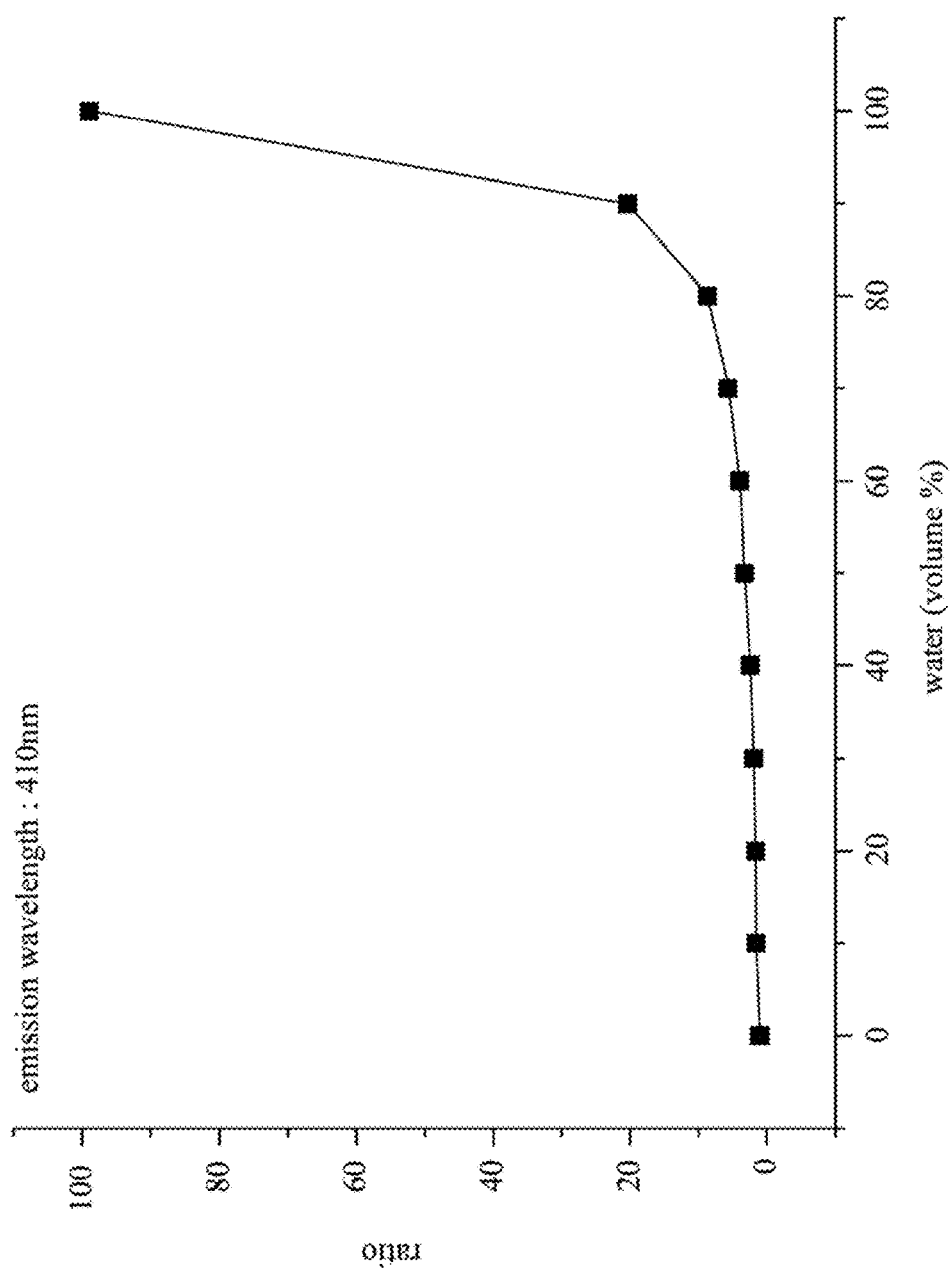
FIG. 16 depicts a ratio of the fluorescence intensity between Experimental Examples 1502 to 1511 and Experimental Example 1501, at the emission wavelength of 410 nm.

FIG. 15 illustrates a fluorescence intensity and an emission wavelength of the water-soluble peptide fluorescence material of formula (III-30) in co-solvents having different proportions of water and dimethyl sulfoxide. In Experimental Example 1501, 1502, 1503, 1504, 1505, 1506, 1507, 1508, 1509, 1510 and 1511, water respectively has 0, 10, 20, 30, 40, 50, 60, 70, 80, 90 and 100% of a total volume of the co-solvent. As shown in FIG. 15, the water-soluble peptide fluorescence material of formula (III-30) has low fluorescence intensity (lower than 100 fluorescent units) in co-solvents of Experimental Examples 1501 to 1509. As such, no significant fluorescence marker is shown, so it is difficult to observe apparent fluorescence visually. While a volume ratio of water is increased to 90% (Experimental Example 1510), the fluorescence intensity is significantly increased to 200 fluorescent units. The volume ratio of water is further increased to 99%, and the fluorescence intensity of Experimental Example 1511 is sharply increased to about 700 fluorescent units, so as to provide a more obvious fluorescence marker. Accordingly, the fluorescence intensity of the water-soluble peptide fluorescence material of formula (III-30) is increased corresponding to the increase of the volume ratio of water and has a phenomenon of aggregation-induced emission in water. In addition, the water-soluble peptide fluorescence material of formula (III-30) has the emission wavelength of about 400 to 425 nm, so the observed fluorescence has a color of blue violet. FIG. 16 depicts a ratio of the fluorescence intensity between Experimental Examples 1502 to 1511 and Experimental Example 1501, at the emission wavelength of 410 nm. As shown in FIG. 16, the fluorescence intensity of Experimental Example 1511 is 100 times of the fluorescence intensity of Experimental Example 1501.

The product of Embodiment 31 has a structure of formula including a peptide sequence Phe-Ile-Lys-Val-Ala-Val (SEQ ID NO: 8) (III-31):

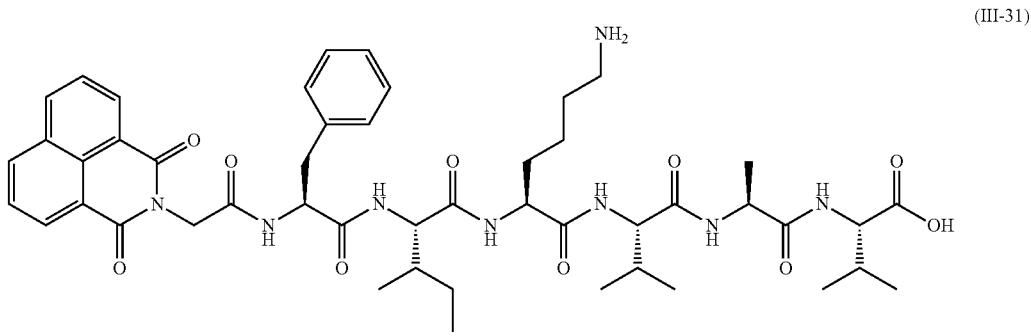 [SMILES: CCC(C)[C@H](NC(=O)[C@H](Cc1ccccc1)NC(=O)CN1C(=O)c2cccc3cccc(c23)C1=O)C(=O)N[C@@H](CCCCN)C(=O)N[C@H](C(=O)N[C@@H](C)C(=O)N[C@H](C(=O)O)C(C)C)C(C)C]

(III-31)

The NMR spectroscopy of the product in Embodiment 31 is shown below:

¹H NMR (300 MHz, DMSO) δ: 0.75-1.00 (m, 18H), 1.05-1.15 (m, 1H), 1.23 (d, J=7.2, 3H), 1.30-1.40, 1.40-1.60, 1.60-1.80 (m, 2H, 4H, 2H), 1.90-2.15 (m, 2H), 2.70-2.90 (m, 3H), 3.00-3.10 (m, 1H), 4.10-4.30 (m, 3H), 4.30-4.50 (m, 2H), 4.55-4.70 (m, 3H), 7.20-7.35 (m, 5H), 7.60-7.85 (m, 4H), 7.85-8.00 (m, 4H), 8.00-8.15 (m, 2H), 8.45-8.60 (m, 5H);

¹³C NMR (75 MHz, DMSO) δ=12.1, 16.1, 16.3, 18.8, 19.1, 20.0, 20.1, 23.2, 25.2, 27.6, 30.9, 31.7, 32.2, 37.7, 38.1, 43.2, 44.7, 48.8, 53.2, 54.7, 58.0, 58.2, 65.9, 122.9, 127.2, 128.2, 128.4, 129.0, 130.3, 131.8, 132.3, 135.5, 138.7, 164.2, 167.6, 171.3, 171.6, 171.7, 172.2, 173.2, 173.8;

MS [ESI⁻]: m/z (%): expected value: 912.47, experimental value: 913.5[M-H]⁻.

Given the above, the conjugated polymer of the present disclosure includes side chains of a tertiary amine group or a quaternary ammonium salt group. When the conjugated polymer of the present disclosure includes the side chains of the tertiary amine group, the conjugated polymer has a good hole-transporting property and water/alcohol solubility. Hence, when fabricating a layered structure, problems of mutual dissolution between different layers can be prevented due to the immiscibility between water/alcohol and the organic solvent for materials in other layers. This conjugated polymer can be used as hole-transporting material. Moreover, since this kind of the conjugated polymer has a good hole-transporting property, it can also be used as a solid electrolyte. When the conjugated polymer of the present disclosure includes the side chains of the quaternary ammonium salt group, the conjugated polymer can be doped to have a good conductive property, and can be used as a conductive polymer. Besides, the conjugated polymer with the quaternary ammonium salt group can be used for the modification of ITO to reduce the work function of the ITO.

The embodiments of the present disclosure discussed above have various advantages, which are summarized below. The water-soluble peptide fluorescence material has a characteristic of aggregation-induced emission (AIE) by changing a nitrogen heterocycle on naphthalimide, so as to generate fluorescence of different colors. In addition, an amino acid sequence of the water-soluble peptide fluorescence material could be changed to develop color in acid, neutral or weak base environment. Furthermore, hydrogen bonds of the amino acid make the water-soluble peptide fluorescence material have characteristic of aggregation-induced emission in water, and the water-soluble peptide fluorescence material is able to form a film at room temperature, so additional initiator or heating process are not necessary. Summarize above points, the water-soluble peptide fluorescence material of the present disclosure has advantages of excellent image recognition, low toxicity to cells and low costs, and thus could generally acts as a fluorescence probe in application of cell image, organelle image, pharmaceutical carrier image and cancer cell detection.

Although the present disclosure has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A water-soluble peptide fluorescence material having a structure of formula (I):

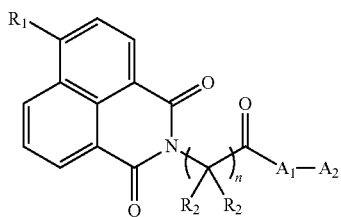
(I)

in formula (I), wherein n is an integer greater than or equal to 1,
$R_1$ is selected from the group consisting of pyrrolidine, piperidine, azepane and azocane,
$R_2$ is independently selected from hydrogen or alkyl, and
$A_1$ is polymerized by at least one amino acid monomer and having a structure of formula (II):

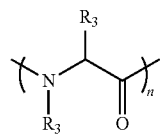
(II)

in formula (II), wherein m is an integer greater than or equal to 1, $R_3$ in each of the amino acid monomers of $A_1$ is independently selected from hydrogen, alkyl, aralkyl, alkylthioaalkyl, hydroxyaralky, heteroaralkyl, carboxylalkyl, or guanidinylalkyl, $A_2$ is —$OR_5$ or —$N(R_4)_2$, wherein $R_4$ is independently selected from hydrogen, alkyl, aralkyl, alkylthioaalkyl, hydroxyaralky, heteroaralkyl, carboxylalkyl, guanidinylalkyl, monoglycosyl, biglycosyl, or oligosaccharyl, and $R_5$ is hydrogen, alkyl, aralkyl, alkylthioaalkyl, hydroxyaralky, heteroaralkyl, carboxylalkyl, or guanidinylalkyl.

2. The water-soluble peptide fluorescence material of claim 1, wherein $R_2$ is an alkyl group of 1-16 carbon atoms.

3. The water-soluble peptide fluorescence material of claim 1, wherein m is the integer of from 1 to 20.

4. The water-soluble peptide fluorescence material of claim 1, wherein n is the integer of from 1 to 10.

5. The water-soluble peptide fluorescence material of claim 1, wherein the monoglycosyl is fructosyl or galactosyl, the biglycosyl is mannosyl, and the oligosaccharyl is oligonucleic acid.

* * * * *

UNITED STATES PATENT AND TRADEMARK OFFICE
CERTIFICATE OF CORRECTION

PATENT NO. : 10,222,381 B2  
APPLICATION NO. : 15/083298  
DATED : March 5, 2019  
INVENTOR(S) : Hsin-Chieh Lin and Shu-Min Hsu It is certified that error appears in the above-identified patent and that said Letters Patent is hereby corrected as shown below:

In the Claims

Column 47, Line 25, Claim 1, delete, " 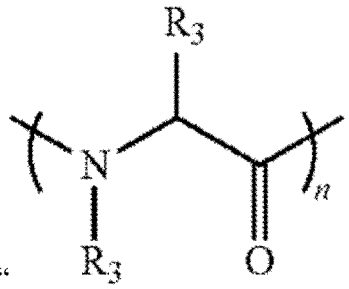 " and insert

-- 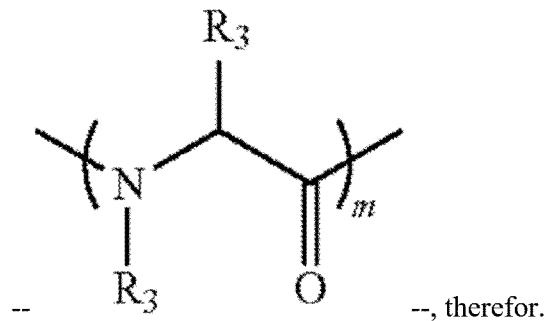 --, therefor.

Signed and Sealed this  
Twenty-second Day of December, 2020

Andrei Iancu  
*Director of the United States Patent and Trademark Office*

SEQUENCE LISTING

```
<160> NUMBER OF SEQ ID NOS: 8

<210> SEQ ID NO 1
<211> LENGTH: 4
<212> TYPE: PRT
<213> ORGANISM: Artificial Sequence
<220> FEATURE:
<223> OTHER INFORMATION: Synthetic peptide

<400> SEQUENCE: 1

Gly Gly Gly Tyr
1

<210> SEQ ID NO 2
<211> LENGTH: 4
<212> TYPE: PRT
<213> ORGANISM: Artificial Sequence
<220> FEATURE:
<223> OTHER INFORMATION: Synthetic peptide

<400> SEQUENCE: 2

Phe Arg Gly Asp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic peptide

<400> SEQUENCE: 3

Phe Asp Asp Asp
1

<210> SEQ ID NO 4
<211> LENGTH: 4
<212> TYPE: PRT
```

```
<213> ORGANISM: Artificial Sequence
<220> FEATURE:
<223> OTHER INFORMATION: Synthetic peptide

<400> SEQUENCE: 4

Phe Glu Glu Glu
1

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Phe Asp Gly Glu Ala
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic peptide

<400> SEQUENCE: 6

Phe Asp Gly Glu Ala
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Gly Gly Gly Gly Gly Tyr
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Phe Ile Lys Val Ala Val
1               5
```